US009586998B2

(12) United States Patent
Gall et al.

(10) Patent No.: US 9,586,998 B2
(45) **Date of Patent: *Mar. 7, 2017**

(54) METHODS OF PROPAGATING MONKEY ADENOVIRAL VECTORS

(71) Applicant: GenVec, Inc., Gaithersburg, MD (US)

(72) Inventors: Jason Gall, Germantown, MD (US); Douglas Brough, Gaithersburg, MD (US); Christoph Kahl, Portland, OR (US); Duncan McVey, Derwood, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,910

(22) Filed: Aug. 4, 2015

(65) Prior Publication Data

US 2015/0329834 A1 Nov. 19, 2015

Related U.S. Application Data

(62) Division of application No. 13/508,659, filed as application No. PCT/US2010/055991 on Nov. 9, 2010, now Pat. No. 9,133,248.

(60) Provisional application No. 61/259,343, filed on Nov. 9, 2009.

(51) Int. Cl.

*C07K 14/005* (2006.01)
*C12N 15/86* (2006.01)
*C12N 7/00* (2006.01)

(52) U.S. Cl.

CPC .............. *C07K 14/005* (2013.01); *C12N 7/00* (2013.01); *C12N 15/86* (2013.01); *C12N 2710/10322* (2013.01); *C12N 2710/10332* (2013.01); *C12N 2710/10343* (2013.01); *C12N 2710/10352* (2013.01)

(58) Field of Classification Search

None

See application file for complete search history.

(56) References Cited

U.S. PATENT DOCUMENTS 5,851,806 A 12/1998 Kovesdi et al.
6,391,612 B1 5/2002 Bruder et al.
6,482,616 B1 11/2002 Kovesdi et al.
6,677,156 B2 1/2004 Brough et al.
6,682,929 B2 1/2004 Brough et al.
6,913,927 B2 7/2005 Brough et al.
7,070,930 B2 7/2006 McVey et al.
7,214,368 B2 5/2007 Rasmussen et al.
8,323,663 B2 12/2012 Brough et al.
9,133,248 B2 * 9/2015 Gall .................... C07K 14/005
2002/0004040 A1 1/2002 Kovesdi et al.
2002/0031831 A1 3/2002 Kovesdi et al.
2003/0017595 A1 1/2003 Brough et al.
2003/0040100 A1 2/2003 Brough et al.
2003/0054553 A1 3/2003 Brough et al.
2004/0063203 A1 4/2004 Brough et al.
2004/0136963 A1 * 7/2004 Wilson ................ C07K 14/005 424/93.2
2006/0211115 A1 9/2006 Roy et al.
2008/0233650 A1 9/2008 Gall et al.
2009/0215871 A1 8/2009 Wilson et al.
2010/0247621 A1 9/2010 Graham et al.

FOREIGN PATENT DOCUMENTS

JP 2005511035 4/2005
JP 2007518414 7/2007
JP 2007525197 9/2007
WO 03/046124 6/2003
WO 03/104467 12/2003
WO 2005/071093 8/2005
WO 2009/073104 6/2009
WO 2010/086189 8/2010

OTHER PUBLICATIONS

Maranga et al., Characterization of Changes in PER.C6TM Cellular Metabolism During Growth and Propagation of a Replication-Deficient Adenovirus Vector, 2005, Biotechnology and Bioengineering, vol. 90, No. 5, pp. 645-655.*

Roy et al., Rescue of chimeric adenoviral vectors to expand the serotype repertoire, Journal of Virological Methods, 141: 14-21 (2007).

Tatsis et al., Chimpanzee-origin adenovirus vectors as vaccine carriers, Gene Therapy, 13: 421-429 (2006).

Altstein et al., Interaction between Human and Simian Adenoviruses in Simian Cells: Complementation, Phenotypic Mixing and Formation of Monkey Cell "Adapted" Virions, Virology, 35: 248-254 (1968).

Grinenko et al., Interaction of Human and Simian Adenoviruses in Human Cells: Complementation, Transcapsidation, and Formation of Defective Adeno-Adeno Hybrids, Molecular Genetics, 5: 25-31 (2004).

Hull et al., New Viral Agents Recovered from Tissue Cultures of Monkey Kidney Cells, AM. J. HYG., 68: 31-44 (1958).

Altstein et al. Hybrid of Human and Monkey Adenoviruses, Journal of Virology, 2: 488-493 (1968).

Grinenko et al., Hybrids of Human and Monkey Adenoviruses (Adeno-Adeno Hybrids) that can Reproduce in Monkey Cells: Biological and Molecular Genetic Peculiarities, Russian Journal of Genetics, 39: 597-603 (2003).

(Continued)

*Primary Examiner* — Benjamin P Blumel

(74) *Attorney, Agent, or Firm* — Nevrivy Patent Law Group P.L.L.C.

(57) ABSTRACT

The invention provides methods for propagating a monkey adenovirus in a cell, including a human cell, comprising one or more gene products isolated from a human adenovirus. Also provided are methods for propagating wherein the monkey adenovirus comprises a nucleic acid sequence encoding a human adenovirus gene product. The invention further provides a monkey adenovirus, including a replication-deficient monkey adenovirus, obtained by such propagation methods.

10 Claims, 3 Drawing Sheets

(56) References Cited

OTHER PUBLICATIONS

Savitskaya et al., The Role of Adenoviral Gene E4 in Species-Specific Adenoviral Reproduction, Doklady Biochemistry, 375: 242-244 (2000).

Roy et al., Isolation and Characterization of Adenoviruses Persistently Shed from the Gastrointestinal Tract of Non-Human Primates, PLOS Pathogens 5(7):e10000503 (Jul. 2009).

Corresponding English Abstract for JP 2007525197 published Sep. 6, 2007.

Corresponding English Abstract for JP 2007518414 published Jul. 12, 2007.

Corresponding English Abstract for JP 2005511035 published Apr. 28, 2005.

International Preliminary Report on Patentability and Written Opinion for PCT/US2010/055991 issued May 15, 2012.

International Search Report for PCT/US2010/055991 issued Jun. 30, 2011.

Office Action (Decision of Rejection) in corresponding application JP2012-538080 dated Nov. 10, 2015 with English language translation.

Office Action (Notice of Reasons for Rejection) in corresponding application JP2012-538080 dated Jan. 27, 2015 with English language translation.

Office Action (Third Office Action) in corresponding application CN2010800610017 dated Dec. 16, 2014 with English language translation.

Office Action (Second Office Action) in corresponding application CN2010800610017 dated Mar. 19, 2014 with English language translation.

English language translation of Office Action (First Office Action) in corresponding application CN2010800610017 dated May 13, 2013.

Office Action in corresponding application EP10782478.1 dated Nov. 26, 2011.

Office Action in corresponding application EP10782478.1 dated Jun. 27, 2011.

Office Action in corresponding application EP10782478.1 dated Feb. 20, 2013.

European Search Report and European Search Opinion in corresponding application EP14192324 dated Feb. 27, 2015.

Havenga et al., Novel replication-incompetent adenoviral B-group vectors: high vector stability and yield in PER.C6 cells, The Role of Adenoviral Gene E4 in Species-Specific Adenoviral Reproduction, Journal of General Virology, 87: 2135-2143 (2006).

Office Action in parent patent application U.S. Appl. No. 13/508,659 mailed Nov. 5, 2013.

Office Action in parent patent application U.S. Appl. No. 13/508,659 mailed Jun. 3, 2014.

* cited by examiner

METHODS OF PROPAGATING MONKEY ADENOVIRAL VECTORS

CROSS REFERENCE TO RELATED APPLICATIONS

This application is a divisional of U.S. application Ser. No. 13/508,659, which is the U.S. National Stage under 35 U.S.C. 371 of International Application No.: PCT/US2010/055991, filed Nov. 9, 2010, which claims the benefit of U.S. Provisional Appl. No. 61/259,343, filed Nov. 9, 2009, the content of which is incorporated by reference herein in its entirety.

INCORPORATION-BY-REFERENCE OF MATERIAL SUBMITTED ELECTRONICALLY

Incorporated by reference in its entirety herein is a computer-readable nucleotide sequence listing submitted concurrently herewith and identified as follows: One 38,463 Byte ASCII (Text) file named “SEQ_Listing.TXT,” created on Nov. 8, 2010.

FIELD OF THE INVENTION

The present invention relates to monkey adenoviruses, and methods for growing monkey adenoviruses, which enable their use in a variety of applications, including the treatment and prevention of human diseases.

BACKGROUND OF THE INVENTION

Recombinant eukaryotic viral vectors have become a preferred means of gene transfer for many researchers and clinicians. In vivo gene transfer is a strategy in which a nucleic acid, usually in the form of DNA, is administered to effect expression of the protein product of the transferred gene in a location that is beneficial to the recipient. The benefit can be the induction of an immune response to the gene product, i.e., vaccination, or modification of the genetic repertoire of target cells for therapeutic purposes. This can be accomplished efficiently using a recombinant adenoviral vector encoding a so-called “transgene.” Adenoviral vectors have advantages over other vectors commonly employed for gene transfer (e.g., retroviral vectors) since adenoviral vectors (i) can be produced in high titers (i.e., up to $10^{13}$ viral particles/ml); (ii) they efficiently transfer genes to nonreplicating as well as replicating cells; (iii) recombination is rare; (iv) there are no known associations of human malignancies with adenoviral infections despite common human infection with adenoviruses; (v) the adenoviral genome can be manipulated to accommodate foreign genes that range in size; (vi) an adenoviral vector does not insert its DNA into the chromosome of a cell, so its effect is impermanent and unlikely to interfere with the cell's normal function; and (vii) live adenovirus, having as an essential characteristic the ability to replicate, has been safely used as a human vaccine (Straus, In *Adenoviruses*, Pienan Press, New York, N.Y., 451-496 (1984); Horwitz et al., In *Virology,* 2nd Ed., Fields et al., eds., Raven Press, New York, N.Y., 1679-1721 (1990); Berkner, *BioTechniques,* 6: 616 (1988); Chanock et al., *IAMA,* 195: 151 (1966); HajAhmad et al., *J. Virol.,* 57: 267 (1986); and Ballay et al., *EMBO J,* 4: 3861 (1985)). The human adenovirus is one of the most widely used recombinant viral vectors in current viral vectored vaccine and gene therapy protocols.

In terms of general structure, all adenoviruses examined to date are nonenveloped, regular icosahedrons of about 65 to 80 nanometers in diameter. Adenoviruses are comprised of linear, double-stranded DNA that is complexed with core proteins and surrounded by the adenoviral capsid. The proteins of the capsid are the targets of neutralizing antibodies and the different serotypes possess distinct amino acid sequences in the capsid proteins that are on the outside of the viral particle.

Adenoviruses belong to the family Adenoviridae, which is divided into five genera, *Mastadenovirus, Atadenovirus, Siadenovirus, Aviadenovirus*, and *Ichtadenovirus*. The adenoviruses in the genus *Mastadenovirus* infect mammals only and include the human, chimpanzee, and monkey adenoviruses.

Adenoviruses provide an elegant and efficient means of transferring transgenes into cells. However, one problem encountered with the use of adenoviral vectors for gene transfer in vivo is the presence of pre-existing immunity to adenovirus that was acquired by the recipient through natural exposure to the adenoviruses. Primarily, infection with adenovirus throughout life induces the generation of antibodies to antigenic epitopes on adenoviral capsid proteins. If sufficient in titer, the antibodies can limit the efficacy of the adenovirus gene transfer vector. In addition, the administration of an adenovirus vector can induce immunity; thus an adenovirus may not be used more than once as an effective gene transfer vehicle. For instance, animal studies demonstrate that intravenous or local administration (e.g., to the lung, heart or peritoneum) of an adenoviral type 2 or 5 gene transfer vector can result in the production of antibodies directed against the vector which prevent expression from the same serotype vector administered 1 to 2 weeks later (see, e.g., Yei et al., *Gene Therapy,* 1: 192-200 (1994); Zabner et al., *Nat. Gen.,* 6: 75-83 (1994); Setoguchi et al., *Am. J. Respir. Cell. Mol. Biol.,* 10: 369-377 (1994); Kass-Eisler et al., *Gene Therapy,* 1: 395-402 (1994); Kass-Eisler et al., *Gene Therapy,* 3: 154-162 (1996)). This is a drawback in adenoviral-mediated gene transfer, since many uses of an adenoviral vector (e.g., for inducing or boosting the immune response to a pathogen or providing a second dose of a therapeutic) require repeat administration. The mechanism by which antibodies directed against an adenovirus are able to prevent or reduce expression of an adenoviral-encoded gene is unclear. However, the phenomenon is loosely referred to as “neutralization”, and the responsible antibodies are termed “neutralizing antibodies.” Thus, to take full advantage of adenovirus vectors for in vivo gene transfer, novel types of adenoviruses are needed that (1) are not susceptible to neutralization by antibodies directed against another type, and (2) are not susceptible to neutralization by antibodies commonly found in the human population.

There are many different adenoviruses isolated from a broad range of animal hosts and adenoviruses are named by host first isolated from. Host animals from which adenoviruses have been isolated include mammals, birds, snakes, frogs, and fish. The mammalian hosts include, among others, primates such as monkeys, humans, and chimpanzees.

Humans and chimpanzees are very closely related and are grouped together as hominids. In contrast, monkeys are not grouped with humans and chimpanzees because there is a significantly greater evolutionary distance between them. The monkeys diverged between 25 and 35 million years ago from the hominids, whereas humans and chimpanzees diverged only about 7 million years ago (Samonte and Eichler, *Nature Reviews Genetics,* 3: 65-72 (2002)). These similarities and differences between humans, chimpanzees, and monkeys are consistent with documented host range restrictions of adenoviruses.

Many different ways for host range restriction occur. For example, wild-type human adenoviruses do not grow productively on monkey cells. In monkey cells infected with wild-type human adenovirus, the viral early genes are properly expressed (Feldman et al., *J Bacteriol.,* 91: 813-8 (1966); Van der Vliet and Levine, *Nature,* 246: 170-4 (1973)), and viral DNA replication occurs normally (Rapp et al., *J. Bacteria,* 92: 931-6 (1966); Reich et al., *PNAS,* 55: 336-41 (1966); Friedman et al., *J. Virol.,* 5: 586-97 (1970)). However, the expression of several late viral proteins is reduced. The block to late gene expression appears to be due to abnormal production of the viral late mRNAs (Klessig and Anderson, *J. Virol.,* 16: 1650-68 (1975)), and this block can be overcome by a single mutation of the adenovirus DNA Binding Protein (DBP) (Klessig and Grodzicker, *Cell,* 17: 957-66 (1979)). Human adenoviruses that contain this single mutation in the DBP grow productively on monkey cells, suggesting that the key to the monkey/human block is centered on the roles of the DBP during the life cycle of the adenovirus.

In contrast to the monkey/human block are the observations that adenoviruses isolated from chimpanzees do not have a restriction in human cells and can be propagated efficiently (W. P. Rowe et al., *Proc. Soc. Exp. Biol. Med,* 97(2): 465-470 (1958); W. D. Hillis et al., *American Journal of Epidemiology,* 90(4): 344-353 (1969); N. Rogers et al., *Nature,* 216: 446-449 (1967)). In particular, replication of some chimpanzee adenovirus isolates was found to be more efficient in human than in monkey cells (M. Basnight et al., *American Journal of Epidemiology,* 94(2):166-171 (1971)). Adenoviruses isolated from other great apes species, such as gorillas and bonobos, have also recently been shown to grow in human cells (S. Roy et al., *PLoS Pathogens,* 5(7): e1000503 (2009)). Wild-type chimpanzee adenovirus replication in human cells does not require the expression of human adenovirus complementing factors, since E1-expressing cell lines (e.g., human embryonic kidney 293 cells, human retina PER.C6 cells) and non-expressing cell lines (A549 human lung epithelial carcinoma cells) have been used for their propagation (U.S. Pat. No. 6,083,716; S. F. Farina et al., *Journal of Virology,* 74(23):11603-11613 (2001); S. Roy et al, *Virology,* 324: 361-372 (2004); S. Roy et al., *Human Gene Therapy,* 15: 519-530 (2004); E. Fattori et al, *Gene Therapy,* 13(14):1088-1096 (2006); J. Skog et al., *Molecular Therapy,* 15(12): 2140-2145 (2007); D. Peruzzi et al., *Vaccine,* 27(9): 1293-1300 (2009)). The absence of a replication block is consistent with the close evolutionary distance between the human and chimpanzee lineages, which diverged only about 7 million years ago (Samonte & Eichler, *Nature Reviews Genetics,* 3: 65-72 (2002)).

Consistent with the greater divergence of hosts, a host range restriction of monkey adenoviruses for growth on human cells has been described (*Am. J. Hyg.,* 68: 31 (1958); *Virology,* 35: 248 (1968); Savitskaya et al., *Doklady Biochemistry,* 375: 242 (2000); Alstein et al., *JVi,* 2: 488 (1968); *Genetika,* 39(6): 725-31 (June 2003)), and it has been hypothesized that the determinants are partially E4 and possibly E2. Savitskaya et al., supra, reported there was no growth of the monkey adenovirus SV7(C8) (now known as SV16 (ICTV 8$^{th}$ Report, p. 220)) on human embryonic kidney (HEK) cell line 293. Thus, an E1 region from a human adenovirus was not sufficient to alleviate the block to replication. The virus could grow on HEK-293 cells with Ad5 E4 region inserted (VK-10-9 cells). However, the VK-10-9 cells provided only partial alleviation of the replication block since replication was 40-fold lower than on CV1 cells (continuous line of green monkey kidney). This showed there was still a block to monkey virus replication in VK-10-9 cells. The authors concluded that E4 expression was too low, based on E4 ORF3 protein level (Krougliak and Graham, *Hum. Gene Ther.,* 6: 1575 (1995)), and a virus specific product was probably required (Savitskaya et al., supra). The authors then proposed the product might be encoded by the E2A gene, though additional study would be needed to clarify the problem. Savitskaya et al., supra, also notes that low E4 expression could have been the cause or an additional factor from E2A would be required for complete release of the replication block, and additional study was needed to define the causes. Interestingly, although the level of E4 expression in the VK-10-9 cells was reported to be significantly lower than that during wild type Ad5 replication, it was high enough for replication of an E4-deleted human adenovirus type 5 virus to the same level as wild type human Ad5 in HEK-293 cells (Krougliak and Graham 1995), further suggesting that the expression level of E4 was not the complete explanation for the species-specific block. Therefore, while it was believed that more E4 expression and/or an E2A product were required, neither was required. Also, it is apparent that the Ad5 E4 function required for virus growth is separate from that required to overcome host range restriction of monkey adenoviruses on human cells because the E4 requirement for growth is not the same for host range determination. Thus, Savitskaya et al., supra, demonstrates that adenovirus E1 and E4 regions are likely not sufficient for alleviating the species block, and that other regions, in particular that encoding the DBP (E2A), are important.

In addition, in another study, an adenovirus-adenovirus hybrid of human Ad2 and SA7(C8) was shown to be defective for replication, suggesting that human E1 and monkey E4 are not compatible and that human adenovirus E1 is not sufficient for overcoming the host range restriction, which is consistent with the above described results where human E1 expressed from the cell did not change host range (Alstein et al., *JVi,* 2: 488 (1968); Savitskaya et al., supra). A different adenovirus-adenovirus hybrid between Ad2 and SA7(C8) was generated by growth of the two viruses under selection conditions to prevent Ad2 propagation (Grinenko et al., *Molecular Genetics, Microbiology and Virology,* 5:25 (2004)). Growth and selection of the hybrid virus on human cells (HEK-293) yielded a defective virus that had incorporated only the L3 region of SA7(C8). The authors note that both Ad2 E4 and E2A (encoding the DNA binding protein) were present and intact in the defective hybrid, and state that the gene E4 and possibly E2A are involved in the determination of species-specific host range, consistent with the earlier conclusions that more than E4 was required for alleviating the host range restriction. These results showed that only 10% of the Ad2 genome could be removed in order for a monkey-human adenovirus hybrid to grow on human cells, leaving 90% of the Ad2 genome to contain host range determining factors. Therefore, this hybrid did not provide further delineation of human adenovirus products required for growth of monkey adenovirus on human cells. Taken together, these reports showed that E4 plays a role in host range determination but other adenovirus genes also play a role. Furthermore, the E4 region is comprised of at least five known protein products, and despite these studies, the component or components of E4 that may have been necessary for the partial alleviation of the host range block were not identified.

Thus, there remains a need for methods that can alleviate, and even remove, the species-specific block or host range restriction which prevents a monkey adenovirus from propagating or replicating efficiently on human cells. There also remains a need for adenoviruses and adenoviral vectors which are capable of circumventing the pre-existing immunity to adenovirus in humans. The invention provides such methods, adenoviruses and vectors, and methods of using the same.

BRIEF SUMMARY OF THE INVENTION

The invention provides a monkey adenovirus. The monkey adenovirus is capable of propagation in a cell comprising one or more gene products of a human adenovirus.

The invention also provides a method for propagating a monkey adenovirus in a cell, wherein the cell comprises a gene product (and/or an encoding nucleic acid sequence) of a human adenovirus. In one embodiment, the invention provides a cell comprising (a) at least one nucleic acid sequence of the E1 region of a human adenovirus, and (b) at least one nucleic acid sequence of the E4 region of a human adenovirus. In another embodiment, there is provided a method of propagating a monkey adenovirus, which method comprises contacting a cell with the monkey adenovirus. The cell expresses a gene product encoded by one or both of the E1A region and the E1B region of a human adenovirus, and a gene product encoded by a portion of the E4 region consisting essentially of E4 ORF6 of a human adenovirus, whereby the monkey adenovirus is propagated in the cell.

The invention also provides a method for propagating a monkey adenovirus in a cell, wherein the monkey adenovirus comprises a nucleic acid sequence encoding a gene product of a human adenovirus. In one embodiment, the monkey adenovirus comprises (a) at least one nucleic acid sequence of the E1 region of a human adenovirus and (b) at least one nucleic acid sequence of the E4 region of a human adenovirus. In another embodiment, there is provided a method of propagating a monkey adenovirus, which method comprises contacting a cell with the monkey adenovirus. In some embodiments, the monkey adenovirus comprises a nucleic acid sequence encoding one or more gene products of a human adenovirus, wherein the one or more gene products comprise a gene product encoded by a portion of the E4 region responsible for alleviating or overcoming host replication block in human cells, which portion consists essentially of E4 ORF6, and whereby the monkey adenovirus is propagated in the cell. In some embodiments, the one or more gene products also comprise a gene product encoded by one or both of the E1A region and the E1B region of a human adenovirus.

The invention also provides a monkey adenovirus obtained by the propagation methods described herein.

In another aspect, the cell in which the monkey adenovirus is propagated preferably is a human cell, and the monkey adenovirus in certain embodiments is replication-deficient. The human adenovirus preferably is a species C human adenovirus.

The invention provides a number of advantages over the art, including means for addressing the pre-existing immunity concerns in humans to human adenoviruses. The invention also provides greatly improved methods for alleviating or overcoming host range restriction or block against propagation or replication of a monkey adenovirus in human cells. The invention thus enables the substantial growth and use of monkey adenoviruses for a full range of purposes, including most notably the treatment and prevention of disease in humans.

BRIEF DESCRIPTION OF THE DRAWINGS

FIG. 2A depicts production in human cell lines differing in expressed Ad5 factors (A549=no Ad5 factors, A549+Ad5 E4ORF6=Ad5 E4ORF6 factor, 293-ORF6=Ad5 E1 and E4ORF6 factors). FIG. 2B depicts production in human cell lines with Ad5 E1 (293 cells), Ad5 E1+Ad5 E4ORF6, or in a monkey cell line (BSC-1). Data are mean+/−standard deviation.

DETAILED DESCRIPTION OF THE INVENTION

Figure 1:
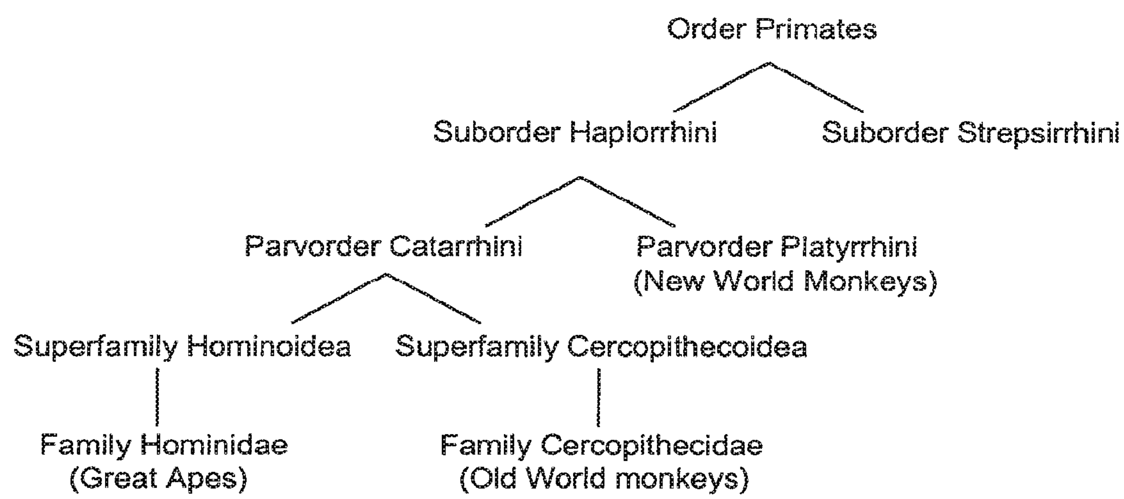
FIG. 1 is a graph illustrating the classification of the order of Primates.

The invention generally provides methods that alleviate or overcome the species-specific block or host range restriction that prevents efficient propagation or replication of a monkey adenovirus in human cells.

The invention also generally provides a monkey adenovirus, the uses for which are accompanied by the advantage of an absence of pre-existing immunity in human populations to monkey adenoviruses.

In one aspect, the invention provides methods for propagating a monkey adenovirus in a cell, wherein the cell expresses one or more gene products of a human adenovirus, and/or wherein the monkey adenovirus comprises a nucleic acid sequence encoding a human adenovirus gene product.

In a second aspect, the invention provides the monkey adenovirus obtained by such propagation methods.

In a third aspect, the invention provides uses for the monkey adenovirus as vectors.

The invention provides a method of propagating a monkey adenovirus involving contacting a cell (e.g., transforming the cell) with the adenovirus. In one embodiment, the cell comprises gene products encoded by one or more of the E1A, E1B, and E4 regions of a human adenovirus. In another embodiment, the cell comprises the gene product (and/or its encoding nucleic acid sequence) responsible for alleviating or overcoming the host replication block of monkey adenoviruses in human cells. In another embodiment, the method comprises contacting a cell with a monkey adenovirus, wherein the cell expresses a gene product encoded by one or both of the E1A region and the E1B region of a human adenovirus, and a gene product encoded by a portion of the E4 region responsible for alleviating or overcoming host replication block in human cells, which portion consists essentially of E4 ORF6, and whereby the monkey adenovirus is propagated in the cell. In another embodiment, the method comprises contacting a cell with a monkey adenovirus, wherein the monkey adenovirus comprises a nucleic acid sequence encoding a human adenovirus gene product, which may include a gene product encoded by one or more of the E1A, E1B, and E4 regions of a human adenovirus, and will include a gene product encoded by the portion of the E4 region responsible for alleviating or overcoming host replication block in human cells. In another embodiment, a method of propagating a monkey adenovirus is provided, which method comprises contacting a cell with the monkey adenovirus. The monkey adenovirus comprises a nucleic acid sequence encoding one or more gene products of a human adenovirus, wherein the one or more gene products comprise a gene product encoded by a portion of the E4 region responsible for alleviating or overcoming host replication block in human cells, which portion consists essentially of E4 ORF6, and whereby the monkey adenovirus is propagated in the cell.

In some embodiments, the cell expresses an E4 region that is responsible for alleviating or overcoming the species-specific block. In some embodiments, the E4 region expressed comprises ORF6. In some embodiments, the E4 region expressed consists essentially of ORF6. In some embodiments, the E4 region expressed consists of ORF6 and no other ORF of the E4 region.

In one embodiment, the cell contacting the monkey adenovirus preferably expresses one or more gene products of a species C human adenovirus, which encompasses a number of human adenoviruses, including a preferred human serotype 5 adenovirus.

Human cells are preferred for propagating the monkey adenovirus, and preferred human cells include an HEK-293 cell or a PerC.6 cell.

The monkey adenovirus also may be replication-deficient. When replication-deficient, the adenovirus requires complementation of one or more of the E1A region, the E1B region, and the E4 region of the adenovirus for propagation. In one embodiment, the monkey adenovirus comprises a deficiency in the E1 region and a deficiency in at least a portion of the E4 region of the adenoviral genome. In a further embodiment, the adenovirus also comprises a deficiency in the E3 region of the adenoviral genome.

In another embodiment, the monkey adenovirus may comprise a heterologous nucleic acid sequence, including a nucleic acid sequence encoding an antigen. The monkey adenovirus preferably comprises a deletion of the E1 region and more preferably also a deletion of at least a portion of the E4 region of the adenovirus, and the heterologous nucleic acid sequence is inserted into the deleted E1 region or the deleted E4 region of the adenovirus.

The monkey adenovirus may be of various serotypes, known or discovered in the future, including the following known serotypes 1, 3, 7, 11, 16, 18, 19, 20, 27, 33, 38, 39, or combinations thereof.

The term "monkey," as used herein, refers to both new world and old world monkeys, and does not include any member of the family Hominidae (e.g., humans, chimpanzees, gorillas, and orangutans, which are also referred to as the "great apes"). New world monkeys include the families Callitrichidae (e.g., marmosets and tamarins), Cebidae (e.g., capuchins and squirrel monkeys), Aotidae (e.g., night or owl monkeys (douroucoulis)), Pitheciidae (e.g., titis, sakis and uakaris), and Atelidae (e.g., howler, spider, and woolly monkeys) (see, e.g., Hershkovitz (ed.), *Living New World Monkeys* (*Platyrrhini*), Volume 1, University of Chicago Pres (1977)). Old world monkeys include animals in the family Cercopithecinae, such as, for example, macaques, baboons, and mangabeys (see, e.g., Whitehead, ed., *Old World Monkeys*, Cambridge University Press (2002)). The term "monkey" also is used synonymously herein with the term "simian." The taxonomy of the order of Primates is illustrated in FIG. 1.

Adenovirus serotypes are differentiated on the basis of neutralization assays. A serotype is defined as one which either exhibits no or limited cross-reaction with other types (see, Fauquet et al. (eds.), *Virus Taxonomy: The Eighth Report of the International Committee on Taxonomy of Viruses*, Academic Press, p. 216 (2005)). The serologically distinguishable serotypes (also referred to as adenovirus "types") are grouped into species. Classically, the species name has reflected the first described host. The lack of cross neutralization combined with a calculated phylogenetic distance of more than 10% separates two serotypes into different species. In addition, species designation depends on other characteristics that differ between serotypes of adenovirus, including host range, DNA hybridization, RFLP analysis, percentage of GC in the genome, oncogenicity in rodents, growth characteristics, possibility of recombination, number of VA RNA genes, hemagglutination, genetic organization of the E3 region, and host range. Simian adenoviruses isolated from monkeys are more distant from both human adenoviruses and chimpanzee adenoviruses. The chimpanzee adenoviruses are closely related to common human adenoviruses of species B and E, so similar that the chimpanzee adenoviruses are grouped within the human species B and E. The limited phylogenic reconstructions for the simian adenoviruses reveal that the simian adenoviruses are quite distinct from the common chimpanzee and human adenoviruses (*Virus Taxonomy: VIIIth Report of the International Committee on Taxonomy of Viruses* (2005)). The phylogeny of adenoviruses that infect primates is disclosed in, e.g., Roy et al., *PLoS Pathog.,* 5(7): e100050. doi: 10.1371/journal.ppat.1000503 (2009).

Various origins, serotypes, or mixtures of serotypes can be used as the source of the viral genome for the simian adenoviral vector (such as those described in, e.g., U.S. Pat. Nos. 7,247,472 and 7,491,508). For instance, a simian adenovirus can be of serotype 1, 3, 6, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, or SAV. In some embodiments, the simian adenoviral vector is a simian adenoviral vector of serotype 3, 6, 7, 11, 16, 18, 19, 20, 27, 33, 38, or 39. In some embodiments, the simian adenoviral vector is of serotype 7, 11, 16, 18, or 38. In one embodiment, the simian adenoviral vector is of serotype 7. These simian adenoviruses, isolated from monkeys, have low sequence homology to human serotype 5 adenovirus, and are more closely related, though quite distinct, from the enteric F and G serotype adenoviruses. They contain two different fiber genes (long and short fibers) instead of one fiber gene, which suggests that they may target the gut mucosa, similar to gut-tropic human adenoviruses, where they are expected to stimulate mucosal immune responses. In addition, comparisons between viral hexon proteins suggest that simian adenovirus serotypes 7, 11, 16, and 38 are distantly related to human adenoviruses, and are categorized more closely to gut-tropic adenoviruses (human Ad40, 41, and 52) than to other groups.

Wild-type simian adenoviruses of any serotype can be isolated using any suitable method. For example, simian adenoviruses can be isolated from monkey biopsy and body secretions, including intestine biopsy, fecal washes, nose washes, lung washes, and other body secretions using standard methods in the art. Wild-type simian adenoviruses also are available from commercial sources, such as the American Type Culture Collection (ATCC, Manassas, Va.).

In some embodiments, the simian adenoviruses are from baboon (e.g., ATCC-VR 275) or Rhesus or African Green monkeys (e.g., ATCC-VR 196, ATCC-VR 201, ATCC-VR 209, ATCC-VR 353, ATCC-VR 355, ATCC-VR 541, ATCC-VR 941, ATCC-VR 942, and ATCC-VR 943).

The invention provides improved monkey adenovirus replication in human cells with preferably complete alleviation of host range block in most cases. The data presented herein confirms that monkey adenoviruses do not grow on human cells and demonstrates equal or even superior growth of monkey adenoviruses on human cells with human adenovirus components compared to monkey cells (see Example 1). Example 1 shows the high productivity of monkey adenoviral progeny on a human cell line with minimal human adenovirus components, comparable or even higher than on monkey cells, in contrast to the 40-fold deficit reported in Savitskaya et al., supra. In some embodiments, the host range restriction can be removed by propagating the monkey virus on human embryonic kidney cell line 293 (HEK-293) along with human adenovirus E4 ORF6 protein (34K) expressed during adenovirus infection. Surprisingly, the expression of the 34 k protein in the HEK-293 cell in Example 1 was too low to be detected, reminiscent to that reported previously for VK-10-9 cells (Krougliak and Graham, *Hum. Gene Ther.,* 6: 1575 (1995)). Thus it was unexpected that the human cell line in Example 1 was equally permissive for monkey adenoviruses as are monkey cells for monkey adenoviruses (data not shown).

Thus, in accordance with the invention, in order to overcome the host range restriction of monkey adenoviruses to grow on human cells, a subset or portion of human adenovirus E4 must be expressed during viral replication in the cell instead of the whole E4 region, as the function of E4 that overcomes the replication block in human cells lies within ORF6. It is possible that the reason for the failure of VK-10-9 cells to fully support monkey adenovirus growth was the presence of inhibitory functions in the human E4 sequences inserted into the cell. Thus, the host range determinant does not include all of E4, and does not include E2A. Rather, the host range determinant is E4 ORF6, and apparently not one of the other factors singly or in combination encoded within E4. In particular, in light of the discovery of E4 ORF6 being sufficient, the data in Savitskaya et al., supra, could be re-interpreted in that less of E4 was required instead of more, and that there may be components in human adenovirus E4, included in VK-10-9 cells, which inhibit growth of monkey adenovirus in human cells.

The identification of the human adenovirus components which permit replication of monkey adenovirus on human cells has many advantages, such as, but not limited to, feasible manufacture of products based on monkey adenovirus. In addition, the ability to reduce the components of E4 required to alleviate the host range block to monkey adenoviruses on human cells has clear advantages compared to requiring all of E4. The simplification of the E4 requirement allows for easier manipulation of the DNA sequences and proper regulation of expression of the E4 sequences. This allows for easier design of systems to allow propagation of monkey viruses on human cells. For example, the subset of human adenovirus E4 sequences can be included in a monkey adenovirus genome, integrated into the genome of a cell or exist extra chromosomally as neither part of the human cell nor the monkey adenovirus. Working with only a subset of E4 sequences that comprise E4 ORF6 allows for easier and more reliable regulation of expression of these sequences. This enhanced control leads to higher yields of monkey adenoviruses which will allow for reduction in cost of goods and expand the commercial and scientific applications that monkey adenoviruses can be used for.

Another advantage of the identification of the human adenovirus components sufficient for allowing replication of monkey adenovirus on human cells is the ability to generate conditionally replicating adenoviruses (CRADs). For example, the inclusion of human adenovirus E1 and E4 ORF6 sequences in the monkey adenovirus, under expression control elements that are specific to a given disease, syndrome, condition, tissue, or cell type, allow for replication of the monkey virus in a controlled fashion only where desired. Applications for CRADs are numerous and include, for example, lysis of tumor cells, expression of a therapeutic gene only under conditions of viral vector replication, and limited-replication vaccines.

Another advantage of the identification of the human adenovirus components sufficient for significant replication of monkey adenovirus on human cells is the ability to generate adenovirus gene transfer vectors where a transgene expression cassette is incorporated into the monkey adenovirus genome. Adenovirus vectors derived from monkey adenoviruses propagated on a human cell line-human adenovirus system have the following advantages: (1) absence of pre-existing immunity in human populations to the monkey adenoviruses, (2) species-specific block to replication for enhanced safety to human populations, and (3) avoids the risk of adventitious xenogeneic pathogens from manufacturing on a non-human cell line. For example, the monkey polyoma virus SV40 was found to contaminate batches of human vaccine product manufactured on monkey cells.

Complementing cell lines for producing the simian adenoviral vector include, but are not limited to, 293 cells (described in, e.g., Graham et al., *J. Gen. Virol.,* 36: 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

Ideally, a replication-deficient simian adenoviral vector is present in a composition, e.g., a pharmaceutical composition, substantially free of replication-competent adenovirus (RCA) contamination (e.g., the composition comprises less than about 1% of replication-competent adenovirus on the basis of the total adenoviruses in the composition). Most desirably, the composition is RCA-free. Adenoviral vector compositions and stocks that are RCA-free are described in U.S. Pat. No. 5,944,106, U.S. Patent Application Publication 2002/0110545 A1, and International Patent Application WO 95/34671.

If the simian adenoviral vector is not replication-deficient, ideally the simian adenoviral vector is manipulated to limit replication of the vector to within a target tissue. For example, the simian adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. In the treatment of viral infections, for example, it can be advantageous to control adenoviral vector replication in, for instance, lymph nodes, to obtain continual antigen production and control immune cell production. Conditionally-replicating adenoviral vectors are described further in U.S. Pat. No. 5,998,205.

One of the utilities of a monkey adenovirus is to deliver proteins or parts of proteins to a cell. One method of delivering the proteins is to tether them to one of the coat proteins of the viral capsid. The capsid can be modified to facilitate this. There are numerous examples of the viral capsid being modified to tether non-adenovirus materials to the capsid. Some of the modifications are proteinaceous in character, while others are not. Examples of substances which can be linked to the adenovirus capsid include antibodies, receptors, PEG, and cross linking chemicals. The viral capsid genes can also be genetically modified to include a foreign gene or portion thereof, so that the foreign gene product is part of the viral capsid protein which becomes part of the viral particle. The effect of the protein can be exerted on the cell with or without it being internalized. If it is not internalized it could activate or inactivate a cell pathway leading to a desired outcome. In addition, if the monkey virus is internalized the protein could elicit an effect on the cell. The protein could also stimulate an immune response potentially to the protein itself. The capsid proteins fiber, hexon, pIX, and penton have all been shown to be able to be modified to include non-adenoviral proteins or portions thereof and or non-proteinacious materials.

Modification of the viral capsid can have additional benefits. The virus's natural tropism can be changed. The virus could be redirected to a new receptor, its interaction with its normal receptor can be abrogated, or its interaction with its normal receptor can be enhanced. Re-directing the monkey adenovirus can increase the desired activity of the virus by directing it to the desired cell type, or it can help avoid a cell type that would yield a non-desirable outcome. The modification can also lead to evasion of the immune system. Multiple capsid proteins can be modified simultaneously.

The coat protein of the adenovirus can be manipulated to alter the binding specificity or recognition of the adenovirus for a receptor on a potential host cell. For adenovirus, such manipulations can include deletion of regions of adenovirus coat proteins (e.g., fiber, penton, or hexon), insertions of various native or non-native ligands into portions of a coat protein, and the like. Manipulation of the coat protein can broaden the range of cells infected by the adenovirus or enable targeting of the adenovirus to a specific cell type.

The simian adenoviral vector can be manipulated to alter the binding specificity or recognition of the adenovirus for a receptor on a potential host cell. For adenovirus, such manipulations can include deletion of regions of adenovirus coat proteins (e.g., fiber, penton, or hexon), insertions of various native or non-native ligands into portions of a coat protein, and the like. Manipulation of the coat protein can broaden the range of cells infected by the simian adenoviral vector or enable targeting of the simian adenoviral vector to a specific cell type. It can also avoid interaction with proteins found in the blood, such as coagulation factor X (FX), which can affect the adenoviral vector biology. Modification of hexon is the preferable method of avoiding the interaction with FX.

Any suitable technique for altering native binding to a host cell, such as native binding of the fiber protein to its cellular receptor, can be employed. For example, differing fiber lengths can be exploited to ablate native binding to cells. This optionally can be accomplished via the addition of a binding sequence to the penton base or fiber knob. This addition of a binding sequence can be done either directly or indirectly via a bispecific or multispecific binding sequence. In an alternative embodiment, the adenoviral fiber protein can be modified to reduce the number of amino acids in the fiber shaft, thereby creating a "short-shafted" fiber (as described in, for example, U.S. Pat. No. 5,962,311). Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of a simian adenoviral vector comprising a short-shafted fiber enables targeting of the simian adenoviral vector to a desired cell-surface receptor by the introduction of a nonnative amino acid sequence either into the penton base or the fiber knob.

In yet another embodiment, the nucleic acid residues encoding amino acid residues associated with native substrate binding can be changed, supplemented, or deleted (see, e.g., International Patent Application Publication WO 00/15823, Einfeld et al., *J. Virol.,* 75(23): 11284-11291 (2001), and van Beusechem et al., *J. Virol.,* 76(6): 2753-2762 (2002)) such that the simian adenoviral vector incorporating the mutated nucleic acid residues (or having the fiber protein encoded thereby) is less able to bind its native substrate.

Any suitable amino acid residue(s) of a fiber protein that mediates or assists in the interaction between the knob and the native cellular receptor can be mutated or removed, so long as the fiber protein is able to trimerize. Similarly, amino acids can be added to the fiber knob as long as the fiber protein retains the ability to trimerize. Suitable residues include amino acids within the exposed loops of the fiber knob domain, such as, for example, the AB loop, the DE loop, the FG loop, and the HI loop.

Any suitable amino acid residue(s) of a penton base protein that mediates or assists in the interaction between the penton base and integrins can be mutated or removed.

Suitable residues include, for example, an RGD amino acid sequence motif located in the hypervariable region of the simian adenovirus penton base protein. The native integrin binding sites on the penton base protein also can be disrupted by modifying the nucleic acid sequence encoding the native RGD motif such that the native RGD amino acid sequence is conformationally inaccessible for binding to an integrin receptor, such as by inserting a DNA sequence into or adjacent to the nucleic acid sequence encoding the adenoviral penton base protein.

The simian adenoviral vector can comprise a fiber protein and a penton base protein that do not bind to their respective native cellular binding sites. Alternatively, the simian adenoviral vector comprises fiber protein and a penton base protein that bind to their respective native cellular binding sites, but with less affinity than the corresponding wild-type coat proteins. The simian adenoviral vector exhibits reduced binding to native cellular binding sites if a modified adenoviral fiber protein and penton base protein binds to their respective native cellular binding sites with at least about 5-fold, 10-fold, 20-fold, 30-fold, 50-fold, or 100-fold less affinity than a non-modified adenoviral fiber protein and penton base protein of the same serotype.

The simian adenoviral vector also can comprise a chimeric coat protein comprising a non-native amino acid sequence that binds a substrate (i.e., a ligand), such as a cellular receptor other than a native cellular receptor. The non-native amino acid sequence of the chimeric adenoviral coat protein allows the simian adenoviral vector comprising the chimeric coat protein to bind and, desirably, infect host cells not naturally infected by a corresponding adenovirus without the non-native amino acid sequence (i.e., host cells not infected by the corresponding wild-type adenovirus), to bind to host cells naturally infected by the corresponding wild-type adenovirus with greater affinity than the corresponding adenovirus without the non-native amino acid sequence, or to bind to particular target cells with greater affinity than non-target cells. A "non-native" amino acid sequence can comprise an amino acid sequence not naturally present in the adenoviral coat protein or an amino acid sequence found in the adenoviral coat but located in a non-native position within the capsid. By "preferentially binds" is meant that the non-native amino acid sequence binds a receptor, such as, for instance, $\alpha v\beta 3$ integrin, with at least about 3-fold greater affinity (e.g., at least about 5-fold, 10-fold, 15-fold, 20-fold, 25-fold, 35-fold, 45-fold, or 50-fold greater affinity) than the non-native ligand binds a different receptor, such as, for instance, $\alpha v\beta 1$ integrin.

The simian adenoviral vector can comprise a chimeric coat protein comprising a non-native amino acid sequence that confers to the chimeric coat protein the ability to bind to an immune cell more efficiently than a wild-type adenoviral coat protein. In particular, the simian adenoviral vector can comprise a chimeric adenoviral fiber protein comprising a non-native amino acid sequence which facilitates uptake of the simian adenoviral vector by immune cells, preferably antigen presenting cells, such as dendritic cells, monocytes, and macrophages. In a preferred embodiment, the simian adenoviral vector comprises a chimeric fiber protein comprising an amino acid sequence (e.g., a non-native amino acid sequence) comprising an RGD motif, which increases transduction efficiency of the simian adenoviral vector into dendritic cells. The ROD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence. The spacer sequence preferably comprises between one and two-hundred amino acids, and can (but need not) have an intended function.

In another embodiment, the simian adenoviral vector can comprise a chimeric virus coat protein that is not selective for a specific type of eukaryotic cell. The chimeric coat protein differs from a wild-type coat protein by an insertion of a non-native amino acid sequence into or in place of an internal coat protein sequence, or attachment of a non-native amino acid sequence to the N- or C-terminus of the coat protein. For example, a ligand comprising about five to about nine lysine residues (preferably seven lysine residues) can be attached to the C-terminus of the adenoviral fiber protein via a non-functional spacer sequence. In this embodiment, the chimeric virus coat protein efficiently binds to a broader range of eukaryotic cells than a wild-type virus coat, such as described in U.S. Pat. No. 6,465,253 and International Patent Application Publication WO 97/20051.

The ability of the simian adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the simian adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, protein IX, VI, or IIIa, etc. Methods for employing such proteins are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525; and 6,951,755, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the non-native amino acid sequence is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to the hexon, preferably it is within a hypervariable region (Crawford-Miksza et al., *J. Virol.,* 70(3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.,* 130: 1189 (1995)). A ligand can even bind non-peptide substrates, such as plastic (e.g., Adey et al., *Gene,* 156: 27 (1995)), biotin (Saggio et al., *Biochem. J.,* 293: 613 (1993)), a DNA sequence (Cheng et al., *Gene,* 171: 1 (1996), and Krook et al., *Biochem. Biophys., Res. Commun.,* 204: 849 (1994)), streptavidin (Geibel et al., *Biochemistry,* 34: 15430 (1995), and Katz, *Biochemistry,* 34: 15421 (1995)), nitrostreptavidin (Balass et al., *Anal. Biochem.,* 243: 264 (1996)), heparin (Wickham et al., *Nature Biotechnol.,* 14: 1570-73 (1996)), and other substrates.

Disruption of native binding of adenoviral coat proteins to a cell surface receptor can also render it less able to interact with the innate or acquired host immune system. Adenoviral vector administration induces inflammation and activates both innate and acquired immune mechanisms. Adenoviral vectors activate antigen-specific (e.g., T-cell dependent) immune responses, which limit the duration of transgene expression following an initial administration of the vector. In addition, exposure to adenoviral vectors stimulates production of neutralizing antibodies by B cells, which can preclude gene expression from subsequent doses of adenoviral vector (Wilson & Kay, *Nat. Med.,* 3(9): 887-889 (1995)). Indeed, the effectiveness of repeated administration of the vector can be severely limited by host immunity. In addition to stimulation of humoral immunity, cell-mediated immune functions are responsible for clearance of the virus from the body. Rapid clearance of the virus is attributed to innate immune mechanisms (see, e.g., Worgall et al., *Human Gene Therapy,* 8: 37-44 (1997)), and likely involves Kupffer cells found within the liver. Thus, by ablating native binding of an adenovirus fiber protein and penton base protein, immune system recognition of an adenoviral vector is diminished, thereby increasing vector tolerance by the host.

A method for evading pre-existing host immunity to adenovirus involves modifying an adenoviral coat protein such that it exhibits reduced recognition by the host immune system. The modified coat protein preferably is a penton, fiber, or hexon protein. Most preferably, the modified coat protein is a hexon protein. The coat protein can be modified in any suitable manner, but is preferably modified by generating diversity in the coat protein. Preferably, such coat protein variants are not recognized by pre-existing host adenovirus-specific neutralizing antibodies. Diversity can be generated using any suitable method known in the art, including, for example, directed evolution (i.e., polynucleotide shuffling) and error-prone PCR (see, e.g., Cadwell, *PCR Meth. Appl.,* 2: 28-33 (1991), Leung et al., *Technique,* 1: 11-15 (1989), and Pritchard et al., *J. Theoretical Biol.,* 234: 497-509 (2005)). Immune avoidance also includes pegylation and the like.

An adenoviral coat protein also can be modified to evade pre-existing host immunity by deleting a region of a coat protein and replacing it with a corresponding region from the coat protein of another adenovirus serotype, particularly a serotype which is less immunogenic in humans. In this regard, amino acid sequences within the fiber protein, the penton base protein, and/or hexon protein can be removed and replaced with corresponding sequences from a different adenovirus serotype. Thus, for example, when the fiber protein is modified to evade pre-existing host immunity, amino acid residues from the knob region of a simian adenovirus fiber protein can be deleted and replaced with corresponding amino acid residues from a simian adenovirus of a different serotype, such as those serotypes described herein. Likewise, when the penton base protein is modified to evade pre-existing host immunity, amino acid residues within the hypervariable region of a simian adenovirus penton base protein can be deleted and replaced with corresponding amino acid residues from a simian adenovirus of a different serotype, such as those serotypes described herein. Preferably, the hexon protein of the simian adenoviral vector is modified in this manner to evade pre-existing host immunity. In this respect, amino acid residues within one or more of the hypervariable regions, which occur in loops of the hexon protein, are removed and replaced with corresponding amino acid residues from a simian adenovirus of a different serotype. An entire loop region can be removed from the hexon protein and replaced with the corresponding loop region of another simian adenovirus serotype. Alternatively, portions of a loop region can be removed from the simian adenoviral vector hexon protein and replaced with the corresponding portion of a hexon loop of another adenovirus serotype (simian or human). One or more hexon loops, or portions thereof, of a simian adenoviral vector can be removed and replaced with the corresponding sequences from any other adenovirus serotype (simian or human), such as those described herein. Methods of modifying hexon proteins are disclosed in, for example, Rux et al., *J. Virol.,* 77:9553-9566 (2003), and U.S. Pat. No. 6,127,525. The hypervariable regions of a hexon protein also can be replaced with random peptide sequences, or peptide sequences derived from a disease-causing pathogen (e.g., HIV).

Modifications to adenovirus coat proteins are described in, for example, U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465, 253; 6,576,456; 6,649,407; 6,740,525; and 6,951,755; and International Patent Applications WO 96/07734, WO 96/26281, WO 97/20051, WO 98/07865, WO 98/07877, WO 98/40509, WO 98/54346, WO 00/15823, WO 01/58940, and WO 01/92549.

Monkey adenovirus can also be used to deliver genetic material to a cell. The genetic material is typically DNA. Any DNA that is inserted in the monkey virus genome is referred to herein as a heterologous nucleic acid sequence or "hDNA." There are a number of functions the hDNA can have that are known in the art. The hDNA can have regulatory properties. Some of the more common elements regulate transcription such as promoters, enhancers, transcriptional terminators, splicing elements, matrix attachment regulatory elements, transcriptional insulators, and poly adenylation sequences to name a few. If RNA is generated from the hDNA it can have a function. Some of the functions are regulatory in nature as shown with siRNA, shRNA, microRNA, anti sense RNA, VA RNA. The RNA can also encode a polypeptide such as a protein. The protein can be native or modified in any fashion that is known in the art. There are many ways to regulate levels of RNA, translation and protein stability that are known in the art.

There are numerous functions the regulatory RNAs and polypeptides can have.

The heterologous nucleic acid sequence preferably encodes an antigen of a pathogen. The pathogen can be a virus, such as respiratory syncitial virus (RSV), human immunodeficiency virus (HIV), foot-and-mouth disease (FMDV), herpes simplex virus (HSV), hepatitis C virus (HCV), ebola virus, or Marburg virus. The pathogen also can be a parasite, such as, for example, a *Plasmodium* parasite, which causes malaria (e.g., *Plasmodium falciparum*). Alternatively, the heterologous nucleic acid sequence can encode, for example, an atonal homolog protein (e.g., HATH1 or MATH1), TNF-α, or pigment epithelium-derived factor (PEDF).

The adenoviral vector of the invention can be replication competent. For example, the adenoviral vector can have a mutation (e.g., a deletion, an insertion, or a substitution) in the adenoviral genome that does not inhibit viral replication in host cells. Preferably, however, the adenoviral vector is replication-deficient. By "replication-deficient" is meant that the adenoviral vector comprises an adenoviral genome that lacks at least one replication-essential gene function (i.e., such that the adenoviral vector does not replicate in typical host cells, especially those in a human patient that could be infected by the adenoviral vector in the course of the inventive method). A deficiency in a gene, gene function, or gene or genomic region, as used herein, is defined as a deletion of sufficient genetic material of the viral genome to impair or obliterate the function of the gene whose nucleic acid sequence was deleted in whole or in part. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2). More preferably, the replication-deficient adenoviral vector comprises an adenoviral genome deficient in at least one replication-essential gene function of one or more regions of the adenoviral genome. Preferably, the adenoviral vector is deficient in at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application WO 00/00628. In some embodiments, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in all or part of the E1A region and all or part of the E1B region. To illustrate but not limit this embodiment, a serotype 35 adenoviral vector can comprise an E1 deletion of nucleotides 570 to 3484. When the adenoviral vector is deficient in at least one replication-essential gene function in only one region of the adenoviral genome (e.g., an E1- or E1/E3-deficient adenoviral vector), the adenoviral vector is referred to as "singly replication-deficient."

The simian adenoviral vector of the invention can be "multiply replication-deficient," meaning that the adenoviral vector is deficient in one or more replication-essential gene functions in each of two or more regions of the adenoviral genome. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector).

By removing all or part of, for example, the E1, E3, and E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector. The adenoviral vector also can comprise multiple (i.e., two or more) nucleic acid sequences encoding the same antigen. Alternatively, the adenoviral vector can comprise multiple nucleic acid sequences encoding two or more different antigens. Each nucleic acid sequence can be operably linked to the same promoter, or to different promoters depending on the expression profile desired by the practitioner, and can be inserted in the same region of the adenoviral genome (e.g., the E4 region) or in different regions of the adenoviral genome.

The simian adenoviral vector, when multiply replication-deficient, especially in replication-essential gene functions of the E1 and E4 regions, preferably includes a spacer sequence to provide viral growth in a complementing cell line similar to that achieved by singly replication-deficient adenoviral vectors, particularly an E1-deficient adenoviral vector. The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer element sequence can be coding or non-coding and native or non-native with respect to the adenoviral genome, but does not restore the replication-essential function to the deficient region. The spacer element preferably is located in the E4 region of the adenoviral genome. The use of a spacer in an adenoviral vector is described in U.S. Pat. No. 5,851,806.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. No. 6,225,113, U.S. Patent Application Publication 2002/0031823 A1, and International Patent Application WO 00/34496. In view of the above, a multiply deficient adenoviral vector (e.g., the at least E4-deficient adenoviral vector) or a second expression vector desirably comprises a nucleic acid sequence encoding a trans-acting factor that modulates the persistence of expression of the nucleic acid sequence. Persistent expression of antigenic DNA can be desired when generating immune tolerance.

The simian adenoviral vector can be deficient in replication-essential gene functions of only the early regions of the adenoviral genome, only the late regions of the adenoviral genome, and both the early and late regions of the adenoviral genome. The simian adenoviral vector also can have essentially the entire adenoviral genome removed, in which case it is preferred that at least either the viral inverted terminal repeats (ITRs) and one or more promoters or the viral ITRs and a packaging signal are left intact (i.e., an adenoviral amplicon). In one embodiment, the simian adenoviral vector of the invention may comprise an adenoviral genome that lacks native nucleic acid sequences which encode adenoviral proteins. Adenoviral genomic elements required for replication and packaging of the adenoviral genome into adenoviral capsid proteins can be retained. Minimal adenoviral vectors lacking adenoviral protein coding sequences are termed "helper-dependent" adenoviral vectors, and often require complementation by helper adenovirus for efficient propagation. Suitable replication-deficient adenoviral vectors, including multiply replication-deficient adenoviral vectors, are disclosed in U.S. Pat. Nos. 5,837,511; 5,851,806; 5,994,106; 6,127,175; and 6,482,616; U.S. Patent Application Publications 2001/0043922 A1, 2002/0004040 A1, 2002/0031831 A1, and 2002/0110545 A1, and International Patent Applications WO 94/28152, WO 95/02697, WO 95/16772, WO 95/34671, WO 96/22378, WO 97/12986, WO 97/21826, and WO 03/022311.

If the adenoviral vector is not replication-deficient, ideally the adenoviral vector is manipulated to limit replication of the vector to within a target tissue. For example, the adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. In autoimmune disease treatment, it can be advantageous to control adenoviral vector replication in, for instance, lymph nodes, to obtain continual antigen production and control immune cell production. Conditionally-replicating adenoviral vectors are described further in U.S. Pat. No. 5,998,205.

It can be advantageous to add large amounts of hDNA in the monkey adenovirus. This can occur for example if large regulatory sequences are needed, multiple transcriptional units are needed or the transcript is large. Since the upper packaging size limit of an adenovirus is approximately 105% of its wild type genome, viruses with larger genomes are difficult to make and are often times unstable.

To overcome this packaging and stability limitation viral DNA sequences can be deleted to accommodate the large amounts of hDNA. There are at least three viral regions (i.e., the E1, E3 and E4 regions) that can be removed from the virus and still be able to generate infectious viral particles. Each of these viral regions is composed of at least one promoter and polyadenylation signal, which encodes for multiple transcripts and proteins. All or portions of these regions can be deleted from the viral genome. It is known in the art that hDNA has been inserted or used to replace each of these regions. These regions can be modified one at a time or in combination to yield an E1, E3 and E4 modified virus. This further expands the flexibility and therefore the utility of the monkey virus.

The removal of the E1, E3 and E4 regions from the virus has additional benefits for the use of monkey adenoviruses. These regions are known to encode multiple regulatory proteins that can alter the host cell directly or stimulate the expression of additional viral proteins. The E1 and E4 regions in particular are known to encode oncogenes. In many applications it is preferred that the virus's genes are not expressed. Some of the benefits of less viral gene expression is improved activity from the added hDNA such as gene expression, avoidance of immune surveillance when the virus is administered to an animal and increased virus dose that can be administered. The ability to increase dosage and improve hDNA gene regulation expands the applications and therefore utility of the monkey virus. Therefore deleting viral DNA will simultaneously expand the amount of hDNA the virus can accommodate and remove harmful sequences from the virus thereby expanding the virus's utility.

The technology described herein supports construction of deleted monkey adenoviruses. As mentioned above the adenovirus E1 region encodes for regulatory proteins. In the absence of E1 function adenoviruses are replication defective (also referred to herein as "replication-deficient"). The Examples below demonstrate that full complementation of the replication deficiency of E1-deleted monkey adenovirus is achieved with human adenovirus E1 and E4ORF6 (see Example 3). Therefore, these regions essential for growth of monkey adenovirus on monkey cells are non-essential for growth in the human cell line-human adenovirus system (Example 3). The proteins encoded by the E3 region are dispensable for virus growth. It is known in the art that adenoviruses with E3 deletions are readily produced even in viruses with E1 and or E4 deletions. Surprisingly, of the multiple known E4 proteins the one responsible for expanded host range of monkey adenoviruses to human cells (ORF6) is also capable of complementing growth of E4 deleted adenoviruses. Expression of both E1 and E4 from the same group C serotype has been shown to support growth of non-species C adenoviruses with E1-, E3-, E4-deletions (Tatsis et al., *Gene Ther.,* 13(5): 421-9 (2006)).

Adenovirus vectors derived from monkey adenoviruses are useful for the following applications: (1) vaccine vectors for infectious disease indications, (2) vaccine vectors for anti-cancer applications, (3) transfer of transgenes encoding therapeutic proteins for acute and chronic disease intervention.

Monkey adenovirus vectors can be used for inducing immune responses (vaccination) in mammals. In this respect, widespread use of human adenoviral vectors is hindered, at least in part, by the immunogenicity of the vector. A majority of the U.S. population has been exposed to wild-type human adenovirus and developed pre-existing immunity to human adenovirus-based gene transfer vectors. As a result, human adenoviral vectors are inactivated by the pre-existing host immune response, thereby reducing the effectiveness of the vector. The neutralization and/or clearance of adenoviral vectors in the body complicates use of these vectors as DNA vaccines. DNA vaccines employ gene transfer vectors to deliver antigen-encoding DNA to host cells. By producing antigenic proteins in vivo, the humoral and cell-mediated arms of the immune system are activated, thereby generating a more complete immune response against the antigen as compared to traditional vaccines wherein foreign proteins are injected into the body. Despite the advantageous characteristics of human adenoviral vectors as gene delivery vehicles, the immunogenicity of the vector prevents efficient repeat dosing, which can be advantageous for "boosting" the immune system against pathogens, and results in only a small fraction of a dose of adenoviral vector delivering its payload to host cells.

The monkey adenoviral vectors will not be subject to neutralization and/or clearance mediated by pre-existing immunity to human adenovirus. Also, the combination of two or more monkey adenoviral vectors will circumvent the inhibition seen with repeated administration of human adenovirus vectors; thus it will be possible to boost the immune system against pathogens. Thus, the monkey adenovirus vectors provide the same advantages of the human adenoviral vectors without their shortcomings.

One embodiment of the adenovirus of the invention comprises a nucleic acid sequence encoding an antigen which is expressed in the mammal to induce an immune response. An "antigen" is a molecule that triggers an immune response in a mammal. An "immune response" can entail, for example, antibody production and/or the activation of immune effector cells. An antigen in the context of the invention can comprise any subunit of any proteinaceous molecule, including a protein or peptide of viral, bacterial, parasitic, fungal, protozoan, prion, cellular, or extracellular origin, which ideally provokes an immune response in a mammal, preferably leading to protective immunity. The antigen also can be a self-antigen, i.e., an autologous protein which the body has mistakenly identified as a foreign invader.

In one embodiment, the antigen is a viral antigen. The viral antigen can be isolated from any virus including, but not limited to, a virus from any of the following viral families: Arenaviridae, Arterivirus, Asiroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus), Herpesviridae (e.g., Human herpesvirus 1, 2, 3, 4, 5, and 6, and Cytomegalovirus), Hypoviridae, Iridoviridae, Leviviridae, Lipothrixviridae, Microviridae, Orthomyxoviridae (e.g., Influenzavirus A and B), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia virus), Reoviridae (e.g., rotavirus), Retroviridae (e.g., lentivirus, such as human immunodeficiency virus (HIV) 1 and HIV 2), Rhabdoviridae, and Totiviridae. In one embodiment, an antigen of the inventive method is a Respiratory Syncytial Virus (RSV) antigen. The antigen can be, for example, an RSV strain A or strain B antigen, such as all or part of the F, G, M, M1, M2, SH, or NS1, or NS2 proteins, or a fusion of all or part of more than one of these proteins. An antigen encoded by the adenoviral vector also can be a retroviral antigen. The retroviral antigen can be, for example, an HIV antigen, such as all or part of the gag, env, or pol proteins. Any clade of HIV is appropriate for antigen selection, including clades A, B, C, MN, and the like. In some embodiments, at least one antigen encoded by the adenoviral vector is a Herpes Simplex Virus 2 (HSV-2) antigen. Suitable SARS virus antigens for the inventive method include, for example, all or part of the UL19, UL47, or gD proteins. The antigenic peptides specifically recited herein are merely exemplary as any viral protein can be used in the context of the invention.

The antigen also can be a parasite antigen such as, but not limited to, a Sporozoan antigen. For example, the nucleic acid sequence can encode a *Plasmodium* antigen, such as all or part of a Circumsporozoite protein, a Sporozoite surface protein, a liver stage antigen, an apical membrane associated protein, or a Merozoite surface protein.

Alternatively or in addition, at least one antigen encoded by the adenoviral vector is a bacterial antigen. The antigen can originate from any bacterium including, but not limited to, *Actinomyces, Anabaena, Bacillus, Bacteroides, Bdellovibrio, Caulobacter, Chlamydia, Chlorobium, Chromatium, Clostridium, Cytophaga, Deinococcus, Escherichia, Halobacterium, Heliobacter, Hyphomicrobium, Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema*. In one embodiment, at least one antigen encoded by the nucleic acid sequence is a *Pseudomonas* antigen or a Heliobacter antigen.

It will be appreciated that an entire, intact viral or bacterial protein is not required to produce an immune response. Indeed, most antigenic epitopes are relatively small in size and, therefore, protein fragments can be sufficient for exposure to the immune system of the mammal. In addition, a fusion protein can be generated between two or more antigenic epitopes of one or more antigens. For example, all or part of HIV gp120 or gp160 can be fused to all or part of the HIV pol protein to generate a more complete immune response against the HIV pathogen compared to that generated by a single epitope. Delivery of fusion proteins by an adenoviral vector to a mammal allows exposure of an immune system to multiple antigens and, accordingly, enables a single vaccine composition to provide immunity against multiple pathogens.

A nucleic acid sequence, including one encoding an antigen, is not limited to a type of nucleic acid sequence or any particular origin. The nucleic acid sequence can be recombinant DNA, can be genomic DNA, can be obtained from a DNA library of potential antigenic epitopes, or can be synthetically generated. The nucleic acid sequence can be present as part of an expression cassette, which additionally comprises the genetic elements required for efficient expression of the nucleic acid sequence and production of the encoded antigen. Ideally, an antigen-encoding nucleic acid sequence is operably linked to a promoter and a polyadenylation sequence as described herein. A promoter can be selected for use in a method of the invention by matching its particular pattern of activity with the desired pattern and level of expression of the antigen(s). For example, an adenoviral vector can comprise two or more nucleic acid sequences that encode different antigens and are operably linked to different promoters displaying distinct expression profiles. For example, a first promoter is selected to mediate an initial peak of antigen production, thereby priming the immune system against an encoded antigen. A second promoter is selected to drive production of the same or different antigen such that expression peaks several days after that of the first promoter, thereby "boosting" the immune system against the antigen. Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. In that antigens can be toxic to eukaryotic cells, it may be advantageous to modify the promoter to decrease activity in complementing cell lines used to propagate the adenoviral vector.

The following examples further illustrate the invention but, of course, should not be construed as in any way limiting its scope.

Example 1

This example demonstrates that monkey adenovirus plaque formation is highly efficient on a human cell line expressing human adenovirus components E1 and E4ORF6.

Monkey adenoviruses are restricted from replication on human cells and human adenovirus factors overcome the restriction. As demonstrated here the invention has two unexpected results: improved growth of monkey adenoviruses on human cells over those that contain the entire E4 region, and superiority in propagating monkey adenoviruses on human cells compared to their native host cell lines recommended for their growth. Two methodologies were used to define growth. Plaque formation was used to determine growth under conditions of very low multiplicity of infection (MOI) and more than one infectious cycle is required to generate a positive result, i.e., a plaque in the cell monolayer. Thus, plaque formation truly demonstrates continuous growth of a virus: single infectious viral particles infect a single cell, full completion of the viral life cycle occurs, followed by infection of neighboring cells by the viral progeny and so on. The second method assesses the number of infectious viral progeny produced from a single round of viral replication. This method is based on synchronous infection of essentially all the cells in the monolayer, known as single-burst growth assessments.

Of all the E4 factors, it is demonstrated herein that ORF6 is sufficient to propagate monkey adenoviruses on human cells. Unexpectedly, the human cell line is superior to monkey cell lines in supporting the ability of monkey adenoviruses to form plaques, a standard method to measure virus growth. Two monkey adenoviruses, SV-11 and SV-38, which were isolated from Rhesus and Vervet monkeys, respectively, were plagued on 293-ORF6, BSC-1, LLC-MK2 (MK2), Vero, and CV-1 cells. All but the 293-ORF6 cell line are derived from monkeys. BSC-1 and MK-2 are the cell lines recommended by the American Type Culture Collection (ATCC) to propagate the viruses on. A serial dilution of both viruses was used to infect each cell line, which were 80% confluent in 60 mm culture dishes. The infection conditions were 500 ul of virus for 1 hour rocked every 15 minutes. The virus was subsequently removed and cells overlaid with EMEM+2% FBS and 0.9% agarose. Fourteen days later plaques were counted. 293-ORF6 cells gave the highest plaquing efficiency being at least ten times better than any of the other cells lines tested (Table 1). Previously it was reported that monkey virus plagued on human cells that contain the entire E4 region from human adenovirus 2 had a plaque formation efficiency 40 times lower compared to CV-1 cells. With this invention there is a clear 400-fold improvement in growth as measured by plaque forming activity. As demonstrated here, the invention has two unexpected results: improved growth of monkey adenoviruses on human cells over those that contain the entire E4 region, and superiority in propagating monkey adenoviruses on human cells compared to their native host cell lines recommended for their growth.

TABLE 1

| Cell Line | Virus | Titer (PFU*/mL) |
|---|---|---|
| BS-C-1 | SV-11 | $1.67 \times 10^8$ |
| CV-1 | SV-11 | $2.89 \times 10^7$ |
| LLC-MK2 | SV-11 | $2.54 \times 10^7$ |
| Vero | SV-11 | $1.94 \times 10^8$ |
| 293-ORF6 | SV-11 | $6.36 \times 10^9$ |
| BSC-1 | SV-38 | $1.27 \times 10^7$ |
| CV-1 | SV-38 | $4.09 \times 10^6$ |
| LLC-MK2 | SV-38 | $1.0 \times 10^7$ |
| Vero | SV-38 | $6.66 \times 10^6$ |
| 293-ORF6 | SV-38 | $2.26 \times 10^8$ |

*plaque forming units

Example 2

This example demonstrates the generation of high-titers of monkey adenovirus viral progeny on a human cell line with human adenovirus species C factors.

Single-burst growth experiments were performed to determine if the combination of human adenovirus E1 and E4 Orf6 was sufficient to overcome the restriction block to monkey adenovirus replication in human cells. Human cells expressing either no Ad5 factors (A549), Ad5 E4ORF6 (A549+Ad5 E4ORF6), Ad5 E1 (293), or Ad5 E1 and E4ORF6 (293-ORF6) were plated in triplicate in 6-well plates at $1.5 \times 10^6$ cells per well. BSC-1 cells derived from African Green Monkey that are permissive for monkey adenovirus replication were plated at $1 \times 10^5$ cells per well. All cells were kept in DMEM with 10% FCS and grown at 37° C., 5% $CO_2$. The next day, cells were infected with $CsCl_2$ gradient-purified monkey adenovirus stocks at an MOI of three (FIG. 2A) or one (FIG. 2B) Focus Forming Unit (FFU)/cell in 300 μl per well for two hours, followed by aspiration and overlay with 3 ml of DMEM with 5% FCS and 100 μM $ZnCl_2$ to permit induction of E4ORF6 expression in A549+Ad5 E4ORF6 and 293-ORF6 cells. Cells were then incubated and harvested at 72 hours post-infection. Virus particles were released from cells by three freeze-thaw cycles consisting of alternating exposures to dry ice and 37° C. water bath. The number of progeny virions in the virus-cell lysates was assessed using the FFU assay described in *Vaccine,* 25: 2074-2084 (2007).

Figure 2A:
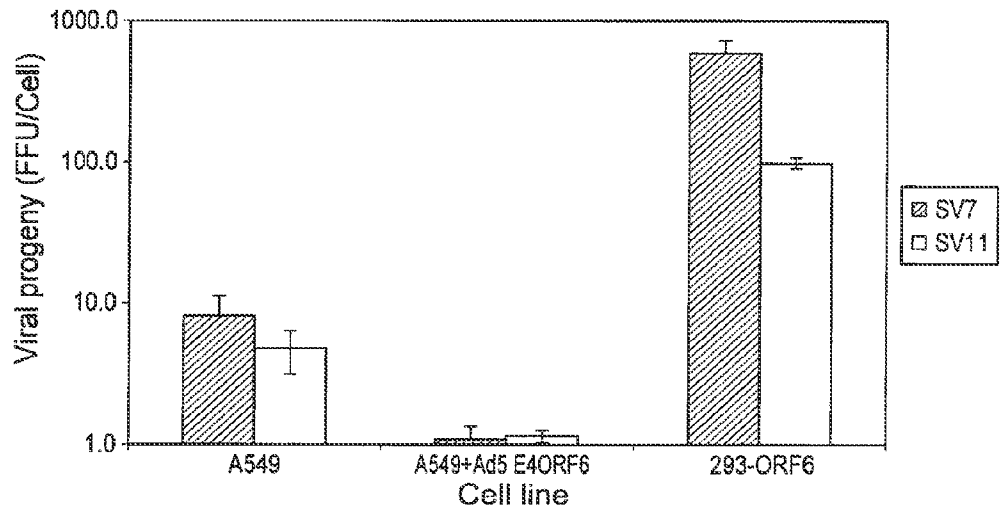
FIG. 2A and FIG. 2B are graphs which illustrate the production of monkey adenovirus progeny under single-burst conditions.
Figure 2B:
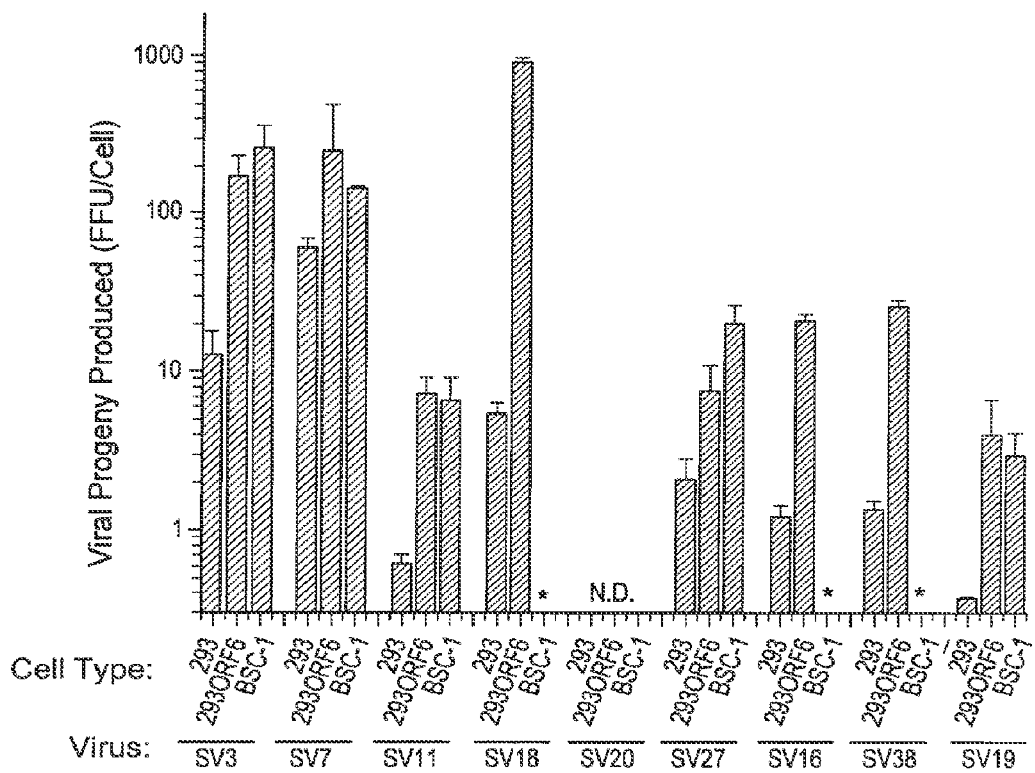

The generation of infectious progeny with monkey adenoviruses on human cell lines was highest with 293-ORF6 cells, compared to A549 and A549 cells expressing Ad5 E4 ORF6 (FIG. 2A). Similarly, generation of viral progeny at an MOI of 1 was at least as efficient on 293-ORF6 cells as on the monkey cell line BSC-1 (FIG. 2B). In some cases, between 10 to 1,000-fold more viral progeny were produced from 293-ORF6 cells as compared to BSC-1 cells. In contrast, monkey adenovirus replication on 293 cells was less efficient than on BSC-1 cells. Therefore, the presence of E1 and E4ORF6 overcame the host replication block in human cells. This was further substantiated with SV-1 which yielded 90,090 particles/cell after purification when grown on 293-ORF6 cells. Finally, generation of infectious progeny on 293-ORF6 cells is up to 1,000-fold higher than on BSC-1 cells, indicating that monkey adenovirus growth on human cells expressing E1 and E4ORF6 is significantly greater than on the native host cell lines recommended for monkey adenovirus growth.

Taken together, plaque formation efficiency and single-burst growth analyses of the monkey adenoviruses demonstrate that monkey adenoviruses can efficiently replicate in 293-ORF6 cells, and that the combined expression of human adenovirus components (Ad5 E1 and E4ORF6) overcomes the human replication block. Furthermore, this was demonstrated with eight monkey adenoviruses, a significant representation of the group.

Example 3

This example demonstrates the construction and propagation of monkey adenovirus vectors with E1 deletions on a human cell line with human adenovirus components.

Seven different monkey adenoviruses from three different species (Vervet, Cynomolgus, and Rhesus macaque) had their E1 region replaced with an expression cassette. The monkey adenoviruses used here are SV-1, SV-7, SV-11, SV-16, SV-18, SV-38, and SV-39 from the ATCC. To facilitate their cloning the left ITR to E1a promoter, pIX promoter region and sequences next to the right ITR of the wild type viruses were determined. The E1 deletions were designed to inactivate the E1a promoter and E1 proteins but retain the pIX viral promoter, viral packaging signal and origin of replication. The identity of these sequences was determined by their homology to known adenovirus genomes, and can be identified using publically available software, for example, as that found at the Berkeley Drosophila Genome Project, National Center for Biotechnology Information and Expert Protein Analysis System. In general, the E1 deletion initiated within 50 base pair (bp) 5' of the E1a promoter TATA box and ended 50 to 300 bp 5' of the pDC promoter. These are only examples of where the deletions can be made, since the deletions can be changed depending on the application of the viral vector. For example the E1 deletion for the SV-38 derived vector retained most of the E1a promoter demonstrating that complete removal of the E1a promoter is not required in order to construct an adenovirus vector.

Although there are multiple ways to construct such viruses, it essentially involves two steps. The desired viral vector genome is generated in bacteria, followed by transfecting the genome into 293-ORF6 cells to make viral particles.

Figure 3:
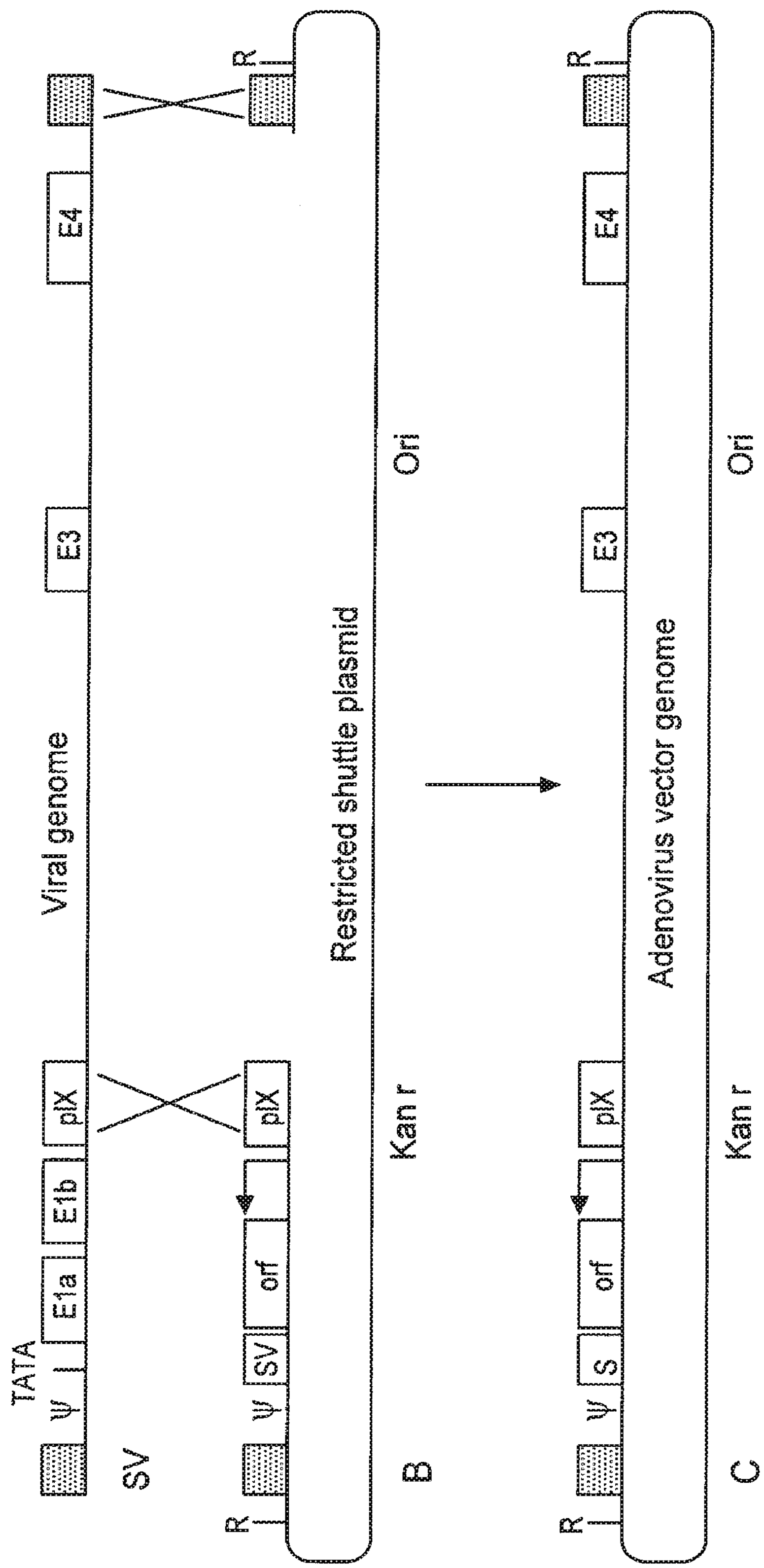
FIG. 3 is a diagram which illustrates a method of constructing monkey adenoviruses with an expression cassette replacing E1. Monkey adenovirus genome (SV) with major regions identified (not to scale): the stippled boxes=ITR, Ψ=packaging signal, TATA=E1a promoter's TATAA box, and coding regions for E1a, E1b, pIX, E3 and E4. B is the recipient plasmid which comprises an expression cassette comprised of a CMV promoter (arrow), open reading frame (orf), and SV40 polyadenylation signal (SV) linearized between the pIX coding sequence and ITR, bacterial origin of replication (Ori) and a gene that encodes Kanamycin (Kan) drug resistance. Homologous recombination (X) between the SV genome and plasmid B results in replacement of the E1 promoter and E1A and E1B coding sequences with the CMV-orf expression cassette. Homologous recombination is generated by transforming recombination competent bacteria BJ5183 with the two DNAs resulting in plasmid C. Bacteria that are Kan resistant are screened, and plasmid C is identified by restriction digest and sequencing. Before the viral genome is transfected into 293-ORF6 cells to generate virus particles, plasmid C is restricted with an endonuclease that recognizes a site (R) outside of the viral genome.

The general procedure to make the viral vector genomes in bacteria is outlined in FIG. 3, or minor variants of it. Using standard molecular biology techniques known in the art, a shuttle plasmid is constructed which comprises the viral ITR (stippled boxes), packaging signal (Ψ), an expression cassette that replaces the E1 region, and pIX sequences, which are followed by the viral right ITR. The expression cassette in this example is comprised of the CMV promoter (arrow), open reading frame (orf) and SV40 polyadenylation signal (SV). The orientation and composition of the expression cassette is illustrative and not intended to be limiting. The plasmid preferably contains a low copy number bacterial origin of replication, such as p15, although other origins of replication can also be used. Inclusion of a gene that provides resistance to an antibiotic such as kanamycin (Kan r), for example, is useful to select for bacteria that harbor the plasmid. To construct the adenovirus vector genome, the remainder of the viral genome from pIX to right ITR is cloned into the shuttle plasmid by homologous recombination. To accomplish this, recombination competent bacteria such as BJ5183 are transformed with both ~50 ng of the shuttle plasmid restricted with an endonuclease between the pIX and right ITR and 100 ng of purified viral genome. It is preferable to have at least 50 bp of homology each between the pIX and right ITR of the shuttle plasmid and viral genome for recombination (X). There are numerous methods known in the art to identity the bacteria with the cloned adenovirus vector genome, including restriction digest, polymerase chain reaction (PCR), and DNA sequencing. Sequencing of the viral hexon gene for example can be used to further confirm the identity of the adenovirus. Homology to the following hexon sequences was used to further confirm the identities of the adenoviruses and their derivatives: SV-1 (SEQ ID NO:22); SV-7 (SEQ ID NO:23); SV-11 (SEQ ID NO:24); SV-16 (SEQ ID NO:25); SV-18 (SEQ ID NO:26); SV-38 (SEQ ID NO:27); SV-39 (SEQ ID NO:28). Once the viral vector genome has been identified, the plasmid is used to transform a $Rec^{A-}$ bacterial strain such as DH10B from which the plasmid is amplified and purified.

Next, the second step, the conversion (rescue) of infectious virus from the genomic plasmids, was conducted as follows. Genomic plasmids were digested with a restriction enzyme to release both Has from the plasmid backbone, purified by phenol:chloroform:isoamyl alcohol extraction and ethanol precipitation, and resuspended in 10 mM Tris, 1 mM EDTA, pH 8.0. The 293-ORF6 cell line, ~$1.5\times10^6$ cells per 60 mm plate, were then transfected with 5 ug of the digested plasmid with Polyfect reagent (Qiagen). Five days post-transfection the cells were harvested, subjected to three freeze-thaw cycles, and the cell lysate was passaged onto fresh cells. Cell-virus lysate was serial passaged in this manner at three to five day intervals until full cytopathic effect (c.p.e.) was observed. Purified adenovirus stocks were generated from infected cells as described in Gall J G, et al. Rescue and production of vaccine and therapeutic adenovirus vectors expressing inhibitory transgenes. *Mol Biotechnol.* 35(3):263-73 (2007), PubMed PMID: 17652790. In brief, infected cells were collected and the culture medium discarded. The cells were lysed in 25 mM Tris pH 7.5, 75 mM NaCl, 5 mM $MgCl_2$ buffer by three freeze/thaw cycles and treated with Benzonase® at 100 units/mL overnight at room temperature. Cesium chloride isopycnic gradient centrifugation was performed and total particle unit titer was determined by absorbance at 260 nm as described in Mittereder, N., et al., Evaluation of the concentration and bioactivity of adenovirus vectors for gene therapy. *J Virol.* 70:7498-7509 (1996). The active particle titers were determined in the fluorescent focus unit (FFU) assay with the Ad2 hexon antibody as described in Gall J G, et al. Rescue and production of vaccine and therapeutic adenovirus vectors expressing inhibitory transgenes. *Mol Biotechnol.* 35(3):

263-73 (2007), PubMed PMID: 17652790; and Lemiale F, et al., Novel adenovirus vaccine vectors based on the enteric-tropic serotype 41. *Vaccine* 25(11):2074-84 (2007), Epub 2006 Nov. 28. PubMed PMID: 17250935, PubMed Central PMCID: PMC2584667. The viral preparations are of high quality with an average ratio of total particles to infectious particles of 49+/−23 (n=6) and high yields, with up to 37,000 particles per cell post-purification. The identity of each virus was confirmed by partial DNA sequencing and diagnostic PCR. The functionality of the expression cassette was confirmed by Western blot analysis.

The identity of the viral sequences used to make the rescue shuttle plasmids described herein and in FIG. 3 are shown below. All sequences are given in left to right orientation of the standard viral genome. In the standard viral genome the E1 region is on the left hand end of the viral genome. The sequence comprising the left hand ITR, packaging signal but devoid of the complete E1a promoter is called “Left hand sequence.” The sequence used for homologous recombination in the pIX region is called “pIX region sequence.” The sequence that is comprised of part of the right ITR that is used for homologous recombination is called “Right sequence.” All sequences are given in the standard 5' to 3' direction.

SV-1: Left hand sequence: (SEQ ID NO:1); pIX region sequence: (SEQ ID NO:2); Right sequence: (SEQ ID NO:3).

SV-7: Left hand sequence: (SEQ ID NO:4); pIX region sequence: (SEQ ID NO:5); Right sequence: (SEQ ID NO:6).

SV-11: Left hand sequence: (SEQ ID NO:7); pIX region sequence: (SEQ ID NO:8); Right sequence: (SEQ ID NO:9).

SV-16: Left hand sequence: (SEQ ID NO:10); pIX region sequence: (SEQ ID NO:11); Right sequence: (SEQ ID NO:12).

SV-18: Left hand sequence: (SEQ ID NO:13); pIX region sequence: (SEQ ID NO:14); Right sequence: (SEQ ID NO:15).

SV-38: Left hand sequence: (SEQ ID NO:16); pIX region sequence: (SEQ ID NO:17); Right sequence: (SEQ ID NO:18).

SV-39: Left hand sequence: (SEQ ID NO:19); pIX region sequence: (SEQ ID NO:20); Right sequence: (SEQ ID NO:21).

Example 4

This example demonstrates that monkey adenoviruses with deletion of E1 region sequences are replication-deficient.

E1-deletions were engineered into the monkey adenoviruses SAV7, SAV11, and SAV16, as described in Example 3. The E1-deletions were designed to remove the promoter of E1A, the entirety of the E1A coding region, the E1B promoter, the E1B 21K protein homolog coding region, and the majority of the 5' end of the E1B 55K homolog coding region. Additionally, an expression cassette, as described in Example 3 and Gall J G, et al., Rescue and production of vaccine and therapeutic adenovirus vectors expressing inhibitory transgenes. *Mol. Biotechnol.* 35(3):263-73 (2007), PubMed PMID: 17652790, without an encoded protein product was inserted into the location of the E1 deletion. To determine if the removal of these sequences changed the replication of the viruses, monkey cells were infected with the viruses and the infectious viral progeny were measured. Two cell lines both of monkey origin were used, and were recommended for propagation of the monkey adenoviruses by the vendor (ATCC). The LLC-MK2 cell line is a kidney line from rhesus macaque (*Macaca mullata*), and the BSC-1 cell line is a kidney line from African green monkey (*Cercopithecus aethiops*). Adherent cultures of the cell lines, plated at $3\times10^5$ cells per well of 6-well plates, were infected with 100 particles per cell of each of the E1-deleted and wild type adenoviruses. At 72 and 96 hours post-infection (hpi), the cells and medium were collected and subjected to three cycles of freezing and thawing (frozen on dry ice~10 minutes, thawed in a 37° C. water bath~10 minutes) to lyse the cells. The cell lysates were assayed for infectious virus in the fluorescent focus unit (FFU) assay as described in Gall J G, et al. Rescue and production of vaccine and therapeutic adenovirus vectors expressing inhibitory transgenes. *Mol. Biotechnol.* 35(3):263-73 (2007), PubMed PMID: 17652790; and Lemiale F, et al., Novel adenovirus vaccine vectors based on the enteric-tropic serotype 41. *Vaccine* 25(11):2074-84 (2007), Epub 2006 Nov. 28. PubMed PMID: 17250935, PubMed Central PMCID: PMC2584667. There were high titers of viral progeny in the lysates generated from cells infected with the wild type viruses (Table 2); thus the cell cultures were permissive to the simian adenoviruses. Importantly, there were no progeny virions detected in the lysates from the cells infected with the E1-deleted simian adenoviruses, with an assay quantitation limit of 25,325 25,875 FFU/mL (minimum of 5 foci per microscopic field, 1013 fields per cell culture well, and undiluted lysate). Comparisons of the maximum titers achieved with each serotype of wild type virus to the quantitation limit shows reduced replication of SAV7 by at least a factor of 19,348; of SAV11 by at least a factor of 10,266; and of SAV16 by at least a factor of 5,133. In addition, there were no foci observed in wells infected with the lysates from the null virus infections, further lowering the assay limit to the limit of detection, 5 FFU/mL. Comparison of the maximum titers achieved with each serotype of wild type virus to the detection limit establishes reduced replication by a factor of $9.8\times10^7$, $5.2\times10^7$, and $2.6\times10^7$ for SAV7, SAV11, and SAV16, respectively. Therefore, the simian adenoviruses with the E1-deletions were replication-deficient.

TABLE 2

Generation of viral progeny (FFU/mL).

| | BSC-1 | | LLC-MK2 | |
|---|---|---|---|---|
| Virus | 72 hpi | 96 hpi | 72 hpi | 96 hpi |
| SAV7 null | 0 | 0 | 0 | 0 |
| SAV11 null | 0 | 0 | 0 | 0 |
| SAV16 null | 0 | 0 | 0 | 0 |
| SAV7 WT | 2.5E+08 | 3.7E+08 | 2.7E+07 | 4.9E+08 |
| SAV11 WT | 2.6E+08 | n.d.* | 1.9E+08 | n.d. |
| SAV16 WT | 5.7E+06 | 1.3E+08 | 2.0E+06 | 5.0E+06 |

*n.d. = not done.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of propagating a monkey adenovirus, which method comprises contacting a cell with the monkey adenovirus, wherein the monkey adenovirus comprises a nucleic acid sequence encoding one or more gene products of a human adenovirus, wherein the one or more gene products comprise a gene product encoded by a portion of the E4 region responsible for alleviating or overcoming host replication block in human cells, which portion consists essentially of E4 ORF6, and whereby the monkey adenovirus is propagated in the cell, wherein the monkey adenovirus further comprises inverted terminal repeat (ITR) sequences from the monkey adenovirus, wherein monkey refers to both new world and old world monkeys, and does not include any member of the family Hominidae.

2. The method of claim 1, wherein the monkey adenovirus comprises a nucleic acid sequence encoding a species C human adenovirus gene product.

3. The method of claim 2, wherein the one or more gene products comprise a gene product encoded by one or both of the E1A region and the E1B region of a human adenovirus.

4. The method of claim 3, wherein the portion of the E4 region is E4 ORF6.

5. The method of claim 4, wherein the cell is a human cell.

6. The method of claim 5, wherein the cell is a HEK-293 cell or a PerC.6 cell.

7. The method of claim 1, wherein the monkey adenovirus is replication-deficient.

8. The method of claim 7, wherein the monkey adenovirus requires complementation of one or more of the E1A region, the E1B region, and the E4 region of the adenoviral genome for propagation.

9. The method of claim 8, wherein the monkey adenovirus comprises a deficiency in the E1 region and a deficiency in at least a portion of the E4 region of the adenoviral genome.

10. The method of claim 9, wherein the monkey adenovirus further comprises a deficiency in the E3 region of the adenoviral genome.

* * * * *

SEQUENCE LISTING

```
<160> NUMBER OF SEQ ID NOS: 28

<210> SEQ ID NO 1
<211> LENGTH: 387
<212> TYPE: DNA
<213> ORGANISM: simian adenovirus SV-1

<400> SEQUENCE: 1

catcatcaat aatatacctt attctggaaa cgtgccaata tgataatgag cggggaggag     60

cgaggcgggg ccggggtgac gtgcggtgac gtggggtgac gcggggtggc gcgagggcgg    120

ggcgggagtg gggaggcgct tagtttttac gtatgcggaa ggaggtttta taccggaagt    180

tgggtaattt gggcgtatac ttgtaagttt tgtgtaattt ggcgcgaaaa ccgggtaatg    240

aggaagttga ggttaatatg tactttttat gactgggcgg aatttctgct gatcagcagt    300

gaactttggg cgctgacggg gaggtttcgc tacgtggcag taccacgaga aggctcaaag    360

gtcccattta ttgtactcct cagcgtt                                        387

<210> SEQ ID NO 2
<211> LENGTH: 561
<212> TYPE: DNA
<213> ORGANISM: simian adenovirus SV-1

<400> SEQUENCE: 2

taaccctgaa cgttaccgag gagctgagga cggaccacca catgctgtct tgcctgcgta     60

ccgactatga atccagcgat gaggagtgag gtgaggggcg gagccacaaa gggtataaag    120

gggcatgagg ggtgggcgcg gtgtttcaaa atgagcggga cgacggacgg caatgcgttt    180

gaggggggag tgttcagccc atatctgaca tctcgtcttc cttcctgggc aggagttcgt    240

cagaatgtag tgggctccac cgtggacgga cggccggtcg cccctgcaaa ttccgccacc    300

ctcacctatg ccaccgtggg atcatcgttg gacactgccg cggcagctgc cgcttctgct    360

gccgcttcta ctgctcgcgg catggcggct gattttggac tatataacca actggccact    420

gcagctgtgg cgtctcggtc tctggttcaa gaagatgccc tgaatgtgat cttgactcgc    480

ctggagatca tgtcacgtcg cctggacgaa ctggctgcgc agatatccca agctaacccc    540

gataccgctt cagaatctta a                                              561

<210> SEQ ID NO 3
<211> LENGTH: 900
<212> TYPE: DNA
<213> ORGANISM: simian adenovirus SV-1

<400> SEQUENCE: 3

acacagtgta aaatgttcag ccaaaaatca ctaagctgct cctttaaaaa gtccagtact     60

tctatattca gttcgtgcaa gtactgaagc aactgtgcgg gaatatgcac agcaaaaaaa    120
```

```
atagggcggc tcagatacat gttgacctaa aataaaaaga atcattaaac taaagaagcc    180

tggcgaacgg tgggatatat gacacgctcc agcagcaggc aagcaaccgg ctgtccccgg    240

gaaccgcggt aaaattcatc cgaatgatta aaaagaacaa cagagacttc ccaccatgta    300

ctcggttgga tctcctgagc acagagcaat acccccctca cattcatatc cgctacagaa    360

aaaaaacgtc ccagataccc agcgggaata tccaacgaca gctgcaaaga cagcaaaaca    420

atccctctgg gagcaatcac aaaatcctcc ggtgaaaaaa gcacatacat attagaataa    480

ccctgttgct ggggcaaaaa ggcccgtcgt cccagcaaat gcacataaat atgttcatca    540

gccattgccc cgtcttaccg cgtaaacagc cacgaaaaaa tcgagctaaa atccacccaa    600

cagcctatag ctatatatac actccaccca atgacgctaa taccgcacca cccacgacca    660

aagttcaccc acacccacaa aacccgcgaa aatccagcgc cgtcagcact tccgcaattt    720

cagtctcaca acgtcacttc cgcgcgcctt ttcactttcc cacacacgcc cttcgcccgc    780

ccgccctcgc gccaccccgc gtcaccccac gtcaccgcac gtcaccccgg ccccgcctcg    840

ctcctccccg ctcattatca tattggcacg tttccagaat aaggtatatt attgatgatg    900


<210> SEQ ID NO 4
<211> LENGTH: 399
<212> TYPE: DNA
<213> ORGANISM: simian adenovirus SV-7

<400> SEQUENCE: 4

catcatcaat aatatacctt attctggaaa cgtgccaata tgataatgag cggggaggag     60

cgaggcgggg ccggggtgac gtgcggtgac gcggggtggc gcgagggcgg ggcgaagggc    120

gcgggtgtgt gtgtgggagg cgcttagttt ttacgtatgc ggaaggaggt tttataccgg    180

aagatgggta atttgggcgt atacttgtaa gttttgtgta atttggcgcg aaaactgggt    240

aatgaggaag ttgaggttaa tatgtacttt ttatgactgg gcggaatttc tgctgatcag    300

cagtgaactt tgggcgctga cggggaggtt tcgctacgtg acagtaccac gagaaggctc    360

aaaggtccca tttattgtac tcttcagcgt tttcgctgg                           399


<210> SEQ ID NO 5
<211> LENGTH: 457
<212> TYPE: DNA
<213> ORGANISM: simian adenovirus SV-7

<400> SEQUENCE: 5

ttgtcctgcc tgcgcaccga ctatgaatcc agcgacgagg agtgaggtga ggggcggagc     60

cacaaagggt ataaaggggc gtgaggggtg ggtgtgatga ttcaaaatga gcgggacgac    120

ggacggcaac gcgtttgagg gtggagtgtt cagcccttat ctgacatctc gtcttccttc    180

ctgggcagga gtgcgtcaga atgtagtggg ctccaccgtg gacggacgac cggtcgcccc    240

tgcaaattcc gccaccctca cctatgccac cgtgggatca tcgttggaca ctgccgcggc    300

agctgccgct tctgctgccg cttctactgc tcgcggcatg gcggctgatt ttggactgta    360

taaccaactg gccactgcag ctgtggcgtc tcggtctctg gttcaagaag atgccctgaa    420

tgtgatcctg actcgcctgg agatcatgtc acgtcgc                             457


<210> SEQ ID NO 6
<211> LENGTH: 300
<212> TYPE: DNA
<213> ORGANISM: simian adenovirus SV-7
```

<400> SEQUENCE: 6
cacccaacag cctatagcta tatatacact ccgcccaatg acgctaatac cgcaccaccc 60
acgaccaaag ttcacccaca cccacaaaac ccgcgaaaat ccagcgccgt cagcacttcc 120
gcaatttcag tctcacaacg tcacttccgc gcgccttttc acattcccac acacacccgc 180
gcccttcgcc ccgccctcgc gccaccccgc gtcaccgcac gtcaccccgg ccccgcctcg 240
ctcctccccg ctcattatca tattggcacg tttccagaat aaggtatatt attgatgatg 300

<210> SEQ ID NO 7
<211> LENGTH: 382
<212> TYPE: DNA
<213> ORGANISM: simian adenovirus SV-11

<400> SEQUENCE: 7
catcatcaat aatatacctt attctggaaa cgtgccaata tgataatgag cggggaggag 60
cgaggcgggg ccggggtgac gtgggagtgg ggagatgggc ggggcgaggt tcgcaggcgg 120
atgcggggag gcgtttagtt tttacgtatg cggaaggagg ttttataccg gaagttgggt 180
aatttgggcg tatacttgta agttttgtgt aatttggcgc gaaaactggg taatgaggaa 240
gttgaggtta atatgtactt tttatgactg ggcggaattt ctgctgatca gcagtgaact 300
ttgggcgctg acggggaggt ttcgctacgt ggcagtacca cgagaaggct caaaggtccc 360
atttattgta ctcctcagcg tt 382

<210> SEQ ID NO 8
<211> LENGTH: 201
<212> TYPE: DNA
<213> ORGANISM: simian adenovirus SV-11

<400> SEQUENCE: 8
taaccctgaa cgttaccgag gagctgagga cggaccacca catgctgtct tgcctgcgta 60
ccgactatga atccagcgat gaggagtgag gtgaggggcg gagccacaaa gggtataaag 120
gggcatgagg ggtgggcgcg gtgtttcaaa atgagcggga cgacggacgg caacgcgttt 180
gaggggggag tgttcagtcc a 201

<210> SEQ ID NO 9
<211> LENGTH: 283
<212> TYPE: DNA
<213> ORGANISM: simian adenovirus SV-11

<400> SEQUENCE: 9
ccaatgacgc taaaaccgcg ccacccacga ccaaagttca cccacaccca caaaacccgc 60
gaaaatccag cgccgtcagc acttccgcaa tttcagtctc acaacgtcac ttccgcgcgc 120
cttttcacag tcccacacac acacccgcgc ccttcgcccg ccccgccctc gcgccacccc 180
gcgtcacccc gcgtcaccct cgcgtcaccc cggccccgcc tcgctcctcc ccgctcatta 240
tcatattggc acgtttccag aataaggtat attattgatg atg 283

<210> SEQ ID NO 10
<211> LENGTH: 401
<212> TYPE: DNA
<213> ORGANISM: simian adenovirus SV-16

<400> SEQUENCE: 10
catcatcaat aatatacctt atttgggaac ggtgccaata tgctaatgag gtgggcggag 60
tttggtgacg tatgcggaaa tgggcggagt taggggcggg gtttggcggt aggcgtggct 120

```
gggggagtgt ccgggcgtgg gaacggaagt gacgtagggg gcgcgccgga ggtgacgtcg    180

tgtggggagt tttaaaccgg aagcaaggta ttttaaacgc ttgcaagcgc aattttgtcg    240

gttttggcgc gaaaactgat aaaaagcgga agttcggtta atcattaatt tttacgatag    300

ggaggaatat ttaccgaggg ccggtgaact ttgagcggtg acgcggtggt ttcgttacgt    360

ggcaccacca cgcgactgct caaagtcccc gtttattgtc t                        401
```

<210> SEQ ID NO 11
<211> LENGTH: 590
<212> TYPE: DNA
<213> ORGANISM: simian adenovirus SV-16

<400> SEQUENCE: 11

```
aacgtgaccg aggagctgag ggccgatcac gtgatgctgt cttgcaaccg caccgactat     60

gccaccagcg acgaggagag tgggtgaggt gagtgggcgt gacctgggcg agcctatata    120

aggggcggcg gagggtcttg ggtctattg cctgaaaaat gagcggggtg gcgggagacg    180

cgagcgtgaa ctttcagggc ggagtgttta gcccatattt gacatctcgc cttccagctt    240

gggcaggagt gcgtcagaat gtggtgggct ctaacctgga tggccgcccg gtggccccgg    300

cgaactcctc taccctcacc tacgcgaccg tgggcgcctc accgttggac accgccgctg    360

ccgccgccgc ttcagcagct gcttctacgg ctcgcgttct ggcggcagat ctgggccttt    420

acaaccatct ggcaactacc gctgcggttt cgcggacggt gagagaagag tccatgcagc    480

tggtgttgga acgtctggag ttgctgactc gtcagttgga agagctttcg gcgaaagtgg    540

ctgacttggc cgccaccttt ccccttcccc cggatgaccc gcagcagtaa               590
```

<210> SEQ ID NO 12
<211> LENGTH: 299
<212> TYPE: DNA
<213> ORGANISM: simian adenovirus SV-16

<400> SEQUENCE: 12

```
aatcagccca caactcaaag gtcactgccg cccgtaaaaa accgccaaaa aatcccgcca     60

aaaagccctt taattcccac agtcacttcc gtatttccac ttcctcaaaa ctccccaaac    120

gacgtcacct ccggcgcgcc ccctacgtca cttccgttcc cacgcccgga cactccccca    180

gccacgccta ccgccaaacc ccgcccctaa ctccgcccat ttccgcatac gtcaccaaac    240

tccgcccacc tcattagcat attggcaccg ttcccaaata aggtatatta ttgatgatg     299
```

<210> SEQ ID NO 13
<211> LENGTH: 458
<212> TYPE: DNA
<213> ORGANISM: simian adenovirus SV-18

<400> SEQUENCE: 13

```
catcatcaat aatatacctt atttgggaac ggtgccaata tgataatgag gaggcggggt     60

taggggtgga gtgagggtgg ggtgcggatg acgcgggcgc ggggcggggt gggagtctga    120

cgtggggcgc ggggtggagc gcgagggtga gggcggggcg agggcggcgg gcgcggcgga    180

attgacgtac acggtagtaa gtttgagcgg aaattaagtg aattgggcgt gttttttgta    240

actttttggt cattttggcg cgaaaactga gtaatgagga agtgagacgg actctgccct    300

tttttacggt tgggagggaa aactgctgat cagcgctgaa ctttgggctc tgacgcggtg    360

gtttccctac gtggcagtgc cacgagaagg ctcaaagtcc tcgttttatt gtgtgctcag    420

cctttttgag ggtatttaaa caccgtcaga ccgtcaag                            458
```

<210> SEQ ID NO 14
<211> LENGTH: 274
<212> TYPE: DNA
<213> ORGANISM: simian adenovirus SV-18

<400> SEQUENCE: 14

```
ccatcagtgt aacctgaccc acaccaaggt gttgctggag acggatgctt tttcgcgagt     60

gaatctgaat ggggtgttcg atctgactat ggagatgtac aagatagtga gatttgatga    120

atcaaagacc cgttgtcgcc cctgcgagtg cggtgccaat cacctgagga tgtatcccgt    180

gaccctgaac gtgacggagg agctgcgccc ggaccaccag atgctgtcct gtctgcgcac    240

cgattacgaa agcagcgatg aggattaaga ggtg                                274
```

<210> SEQ ID NO 15
<211> LENGTH: 125
<212> TYPE: DNA
<213> ORGANISM: simian adenovirus SV-18

<400> SEQUENCE: 15

```
ccacgtcaga ctcccacccc gccccgcgcc cgcgtcatcc gcaccccacc ctcactccac     60

ccctaacccc gcctcctcat tatcatattg gcaccgttcc caaataaggt atattattga    120

tgatg                                                                125
```

<210> SEQ ID NO 16
<211> LENGTH: 382
<212> TYPE: DNA
<213> ORGANISM: simian adenovirus SV-38

<400> SEQUENCE: 16

```
catcatcaat aatatacctt attctggaaa cgtgccaata tgataatgag cggggaggag     60

cgaggcgggg ccggggtgac gtgggagtgg ggagatgggc ggggcgaggt tcgcaggcgg    120

atgtggggag gcgtttagtt tttacgtatg cggaaggagg ttttataccg gaagttgggt    180

aatttgggcg tatacttgta agttttgtgt aatttggcgc gaaaactggg taatgaggaa    240

gttgaggtca atatgtactt tttatgactg ggcggaattt ctgctgatca gcagtgaact    300

ttgggcgctg acggggaggt ttcgctacgt ggcagtacca cgagaaggct caaaggtccc    360

atttattgta ctcctcagcg tt                                             382
```

<210> SEQ ID NO 17
<211> LENGTH: 559
<212> TYPE: DNA
<213> ORGANISM: simian adenovirus SV-38

<400> SEQUENCE: 17

```
gtaaccctga acgttaccga ggagctgagg acggaccacc acatgctgtc ttgcctgcgt     60

accgactatg aatccagcga tgaggagtga ggtgaggggc ggagctacaa agggtataaa    120

ggggcatgag ggtgggcgc ggtgtttcaa aatgagcggg acgacggacg gcaatgcgtt    180

tgagggggga gtgttcagtc catatctgac atctcgtctt ccttcctggg caggagttcg    240

tcagaatgta gtgggctcca ccgtggacgg acgaccggtc gcccctgcga attccgccac    300

cctcacctat gccaccgtgg gatcatcgtt ggacactgcc gcggcagctg ccgcttctgc    360

tgccgcttct actgctcgcg gcatggcggc tgattttgga ctgtataacc aactggccac    420

tgcagctgtg gcgtctcggt ctctggttca agaggatgcc ctgaatgtga tcctgactcg    480
```

```
cctggagatc atgtcacgtc gcctggacga actggctgcg cagatatccc aagctaaccc    540

cgataccact tcagaatct                                                 559


<210> SEQ ID NO 18
<211> LENGTH: 73
<212> TYPE: DNA
<213> ORGANISM: simian adenovirus SV-38

<400> SEQUENCE: 18

ccccggcccc gcctcgctcc tccccgctca ttatcatatt ggcacgtttc cagaataagg     60

tatattattg atg                                                        73


<210> SEQ ID NO 19
<211> LENGTH: 394
<212> TYPE: DNA
<213> ORGANISM: simian adenovirus SV-39

<400> SEQUENCE: 19

catcatcaat ataacaccgc aagatggcga ccgagttaac atgcaaatga ggtgggcgga     60

gttacgcgac ctttgtcttg ggaacgcgga agtgggcgcg gcgggtttcg gggaggagcg    120

cggggcgggg cgggcgtgtc gcgcggcggt gacgcgccgg ggacccggaa attgagtagt    180

ttttattcat tttgcaagtt tttctgtaca ttttggcgcg aaaactgaaa cgaggaagtg    240

aagagtgaaa aatgccgagg tagtcaccgg gtggagatct gacctttgcc gtgtggagtt    300

tacccgctga cgtgtgggtt tcggtctcta ttttttcact gtggttttcc gggtacggcc    360

aaaggtcccc attttacgac tccacctcga ggga                                394


<210> SEQ ID NO 20
<211> LENGTH: 589
<212> TYPE: DNA
<213> ORGANISM: simian adenovirus SV-39

<400> SEQUENCE: 20

ctgtgatggg gatggtgact gaggaggtgc gactggacac tgtcagcact cttgcctgcg     60

ggaggagttt tcttcctcgg acgaggagga ctaggtaggt ggttggggcg tggccagcga    120

gagggtgggc tataaagggg aggtgtcggc tgacgctgtc ttctgttttt caggtaccat    180

gagcggatca agcagccaga ccgcgctgag cttcgacggg gccgtgtaca gccccttctt    240

gacagggcgc ttgcctgcct gggccggagt gcgtcagaat gttaccggtt cgaccgtgga    300

cggacgtccc gtggatccat ctaacgctgc ttctatgcgc tacgctacta tcagcacatc    360

tactctggac agcgccgctg ccgccgcagc cgccacctca gccgctctct ccgccgccaa    420

gatcatggct attaacccaa gcctttacag ccctgtatcc gtggacacct cagccctgga    480

gctttaccgg cgagatctag ctcaagtggt ggaccaactc gcagccgtga gccaacagtt    540

gcagctggtg tcgacccgag tggagcaact ttcccgccct ccccagtaa                589


<210> SEQ ID NO 21
<211> LENGTH: 612
<212> TYPE: DNA
<213> ORGANISM: simian adenovirus SV-39

<400> SEQUENCE: 21

gcaacggttg aggtctccac ataatcagcg cccacaaaaa tcccatctcg aacttgctcg     60

cgtagggagc taaaatggcc agtatagccc catggcaccc gaacgctaat ctgcaagtat    120

atgagagcca ccccattcgg cgggatcaca aaatcagtcg gagaaaacaa cgtatacacc    180
```

```
ccggactgca aaagctgttc aggcaaacgc ccctgcggtc cctctcggta caccagcaaa    240

gcctcgggta aagcagccat gccaagcgct taccgtgcca agagcgactc agacgaaaaa    300

gtgtactgag gcgctcagag cagcggctat atactctacc tgtgacgtca agaaccgaaa    360

gtcaaaagtt cacccggcgc gcccgaaaaa acccgcgaaa atccacccaa aaagcccgcg    420

aaaaacactt ccgtataaaa tttccgggtt accggcgcgt caccgccgcg cgacacgccc    480

gccccgcccc gcgctcctcc ccgaaacccg ccgcgcccac ttccgcgttc ccaagacaaa    540

ggtcgcgtaa ctccgcccac ctcatttgca tgttaactcg gtcgccatct tgcggtgtta    600

tattgatgat ga                                                        612


<210> SEQ ID NO 22
<211> LENGTH: 2796
<212> TYPE: DNA
<213> ORGANISM: simian adenovirus SV-1

<400> SEQUENCE: 22

atggccaccc catcgatgat gccgcagtgg tcttacatgc acatcgccgg gcaggacgcc     60

tcggagtacc tgagccccgg tctcgtgcag ttcgcccgcg ccaccgacac ctacttcagc    120

ttgggaaaca agtttagaaa ccccaccgtg gcccccaccc acgatgtaac cacggaccgc    180

tcgcaaaggc tgaccctgcg ttttgtgccc gtagaccggg aggacaccgc gtactcttac    240

aaagtgcgct acacgctggc cgtaggggac aaccgagtgc tggacatggc cagcacctac    300

tttgacatcc ggggagtgct ggatcgcggt cccagtttta agccctactc gggtaccgcg    360

tacaattccc tggctcccaa gggcgctccc aaccctgcag aatggacgaa ttcagacagc    420

aaagttaaag tgagggcaca ggcgcctttt gttagctcgt atggtgctac agcgattaca    480

aaagagggta ttcaggtggg agtaacctta acagactccg gatcaacacc acagtatgca    540

gataaaacgt atcagcctga gccgcaaatt ggagaactac agtggaacag cgatgttgga    600

accgatgaca aaatagcagg aagagtgcta aagaaaacaa cgcccatgtt cccttgttac    660

ggctcatatg ccaggcccac taatgaaaaa ggaggacagg caacaccgtc cgctagtcaa    720

gacgtgcaaa atcccgaatt acaatttttt gcctctacta atgtcgccaa tacaccaaaa    780

gcagttctat atgcggagga cgtgtcaatt gaagcgccag acactcactt ggtgttcaaa    840

ccaacagtca ctgaaggcat tacaagttca gaggctctac tgacccaaca agctgctccc    900

aaccgtccaa actacatagc ctttagagat aattttattg gtctcatgta ctacaatagc    960

acaggtaaca tgggagtact ggcaggccag gcttctcagc taaatgcagt tgttgacctg   1020

caagacagaa atactgagct gtcctaccaa ctcatgttgg acgccctcgg agaccgcagt   1080

cggtactttt ctatgtggaa ccaagctgtg gatagttacg atcctgatgt aagaatcata   1140

gaaaaccatg gcgtagaaga tgaattgcct aattattgct ttcctttggg aggcatggca   1200

gtaaccgaca cctactcgcc tataaaggtt aatggaggag gcaatggatg ggaagccaat   1260

aacggcgttt tcaccgaaag aggagtggaa ataggttcag ggaacatgtt tgccatggag   1320

attaacctgc aagccaacct atggcgtagc tttctgtact ccaatattgg gctgtacctg   1380

ccagactctc tcaaaatcac tcctgacaac atcacactcc cagagaacaa aaacacctat   1440

cagtatatga acggtcgcgt gacgccaccc gggctggttg acacctacgt taacgtgggc   1500

gcgcgctggt cccccgatgt catggacagt attaaccctt ttaatcacca ccgcaacgcc   1560

ggactccgct accgttccat gctcctggga aacggacgct acgtgccctt ccacatccag   1620

gtgccccaga aattctttgc aattaaaaac ctgctgctgc tccccggttc ctacacctac   1680
```

```
gagtggaact tccgcaagga cgtgaacatg atcttgcaga gctcgctggg caatgacctg   1740

cgagtggacg gggccagcat ccgcttcgac agcatcaacc tgtacgccaa ctttttcccc   1800

atggcccaca acacggcctc caccctggaa gccatgctgc gcaacgacac caacgaccaa   1860

tctttcaacg actacctgtg cgcggccaac atgctgtacc ccatccccgc caacgccacc   1920

agcgtgccca tctccattcc ctctcgcaac tgggcagcct tcaggggctg gagtttcacc   1980

cgcctcaaaa ccaaggagac cccctcgctg ggctccgggt tcgaccccta cttcgtctac   2040

tccggctcca tcccctacct ggacggcacc ttctacctca accatacttt caaaaaggtg   2100

tcaatcatgt tcgactcctc cgtcagctgg cccggcaacg accgtctgct gacgcccaac   2160

gagttcgaaa tcaagcgttc ggtggacggt gaagggtaca acgtggctca gagcaacatg   2220

accaaggact ggttcctgat tcagatgctc agccactaca acatcggcta ccagggcttc   2280

tacgtgcccg aaaattacaa ggaccgcatg tactcttttct tcagaaactt ccaacccatg   2340

agccgccaaa ttgtagattc aacggcttac actaattatc aggatgtgaa actgccatac   2400

cagcataaca actcagggtt cgtgggctac atgggaccca ccatgcgaga ggggcaggcc   2460

tacccggcca actatcccta tcccctgatt ggggccaccg ccgtgcccag cctcacgcag   2520

aaaaagttcc tctgcgaccg ggtgatgtgg aggatcccct tctctagcaa cttcatgtct   2580

atgggctccc tcaccgacct ggggcagaac atgctgtacg ccaactccgc tcacgccttg   2640

gatatgacct ttgaggtgga tcccatggat gagcccacgc ttctctatgt tctgtttgaa   2700

gtcttcgacg tggtgcgcat ccaccagccg caccgcggcg tcatcgaggc cgtctacctg   2760

cgcacacctt tctctgccgg taacgccacc acctaa                             2796
```

```
<210> SEQ ID NO 23
<211> LENGTH: 2766
<212> TYPE: DNA
<213> ORGANISM: simian adenovirus SV-7

<400> SEQUENCE: 23
```

```
atggccaccc catcgatgat gccgcagtgg tcttacatgc acatcgccgg ccaggacgcc     60

tcggagtacc tgagtcccgg cctcgtgcag tttgcccgcg ccaccgacac ctacttcagc    120

ttgggaaaca agtttagaaa ccccaccgtg gcccccaccc acgatgtgac cacggaccgc    180

tcgcagaggc tgaccctgcg ctttgtgccc gtagaccggg aggacaccgc gtactcttac    240

aaagtgcgct acacgttggc cgtaggggac aaccgagtgc tggacatggc cagcacctac    300

tttgacatcc ggggggtgct ggatcggggt cccagcttca agccctattc cggcaccgct    360

tacaactccc tggcccccaa gggagctccc aacccctcgg aatggacgga cacttccgac    420

aacaaactta aagcatatgc tcaggctccc taccagagtc aaggacttac aaaggatggt    480

attcaggttg ggctagttgt gacagagtca ggacaaacac cccaatatgc aaacaaagtg    540

taccaacccg agccacaaat tggggaaaac caatggaatt tagaacaaga agataaagcg    600

gcgggaagag tcctaaagaa agatacccct atgtttccct gctatgggtc atatgccagg    660

cccacaaacg aacaaggagg gcaggcaaaa aaccaagaag tagatttaca gtttttttgcc    720

actccgggcg acacccagaa cacggctaaa gtggtacttt atgctgaaaa tgtcaacctg    780

gaaactccag atactcactt agtgtttaaa cccgatgacg acagcaccag ttcaaaactt    840

cttcttgggc agcaggctgc acctaacaga cccaactaca taggttttag agataatttt    900

attggtttaa tgtactacaa tagcactgga aacatgggcg tgctggccgg acaggcttct    960

caattgaatg ccgtagtcga cttgcaggac agaaacaccg agttgtccta ccagctgatg   1020
```

```
ctggacgcac tgggggatcg cagccgatat ttttcaatgt ggaatcaggc agtagacagc   1080

tatgacccag acgttagaat tatagaaaac cacggagtgg aagacgaact gccaaactat   1140

tgttttcctc tgggaggaat ggtggtgact gacaattaca actctgtgac gcctcaaaat   1200

ggaggcagtg gaaatacatg gcaggcagac aatactacat ttagtcaaag aggagcgcag   1260

attggctccg gaaacatgtt tgccctggaa attaacctac aggccaacct ctggcgcggc   1320

ttcttgtatt ccaatattgg gttgtatctt ccagactctc tgaaaatcac ccccgacaac   1380

atcacgctgc cagaaaacaa aaacacttat cagtacatga acggtcgcgt aacgccaccc   1440

gggctcatag acacctatgt aaacgtgggc gcgcgctggt cccccgatgt catggacagc   1500

attaacccct tcaaccacca ccgtaacgcg ggcttgcgct accgctccat gctcttgggc   1560

aacggccgtt atgtgccttt tcacattcag gtgccccaaa aattctttgc cattaaaaac   1620

ctgctgcttc tccccggttc ctatacctat gagtggaact tccgcaagga tgtcaacatg   1680

atcctgcaga gctcgctggg taatgacctg cgagtggacg gggccagcat acgctttgac   1740

agcattaacc tgtatgccaa ctttttttccc atggcccaca acacggcctc taccctggaa   1800

gccatgctgc gcaacgacac caatgaccag tccttcaacg actacctgtg cgcggctaac   1860

atgctgtacc ccatccccgc caacgccacc agcgtgccca tttctattcc ttctcggaac   1920

tgggctgcct tcaggggctg gagttttact cgcctcaaaa ccaaggagac tccctcgctg   1980

ggctccggtt ttgaccccta ctttgtttac tccggctcca ttccctacct agatggcacc   2040

ttttacctca accacacttt caaaaaggtg tctattatgt ttgactcctc ggttagctgg   2100

cccggcaacg accgcctgct aacgcccaac gagttcgaaa ttaagcgttc cgtggacggt   2160

gaagggtaca acgtggccca gagcaacatg accaaggact ggtttctaat tcaaatgctc   2220

agtcactata atataggtta ccagggcttc tatgtgcccg agaactacaa ggaccgcatg   2280

tactccttct tccgcaactt ccaaccaatg agccggcagg tggtagatac cgtgacttat   2340

acagactaca aagatgtcaa gctcccctac caacacaaca actcagggtt cgtgggctac   2400

atgggaccca ccatgcgaga gggacaggcc tacccggcca actatcccta cccccctgatc   2460

ggagagactg ccgtacccag cctcacgcag aaaaagttcc tctgcgaccg ggtgatgtgg   2520

aggataccct tctctagcaa ctttatgtcg atgggctccc tcaccgacct ggggcagaac   2580

atgctgtacg ccaactccgc tcacgccttg gacatgactt ttgaggtgga tcccatggat   2640

gagcccacgc ttctctatgt tctgtttgaa gtcttcgacg tggtgcgcat ccaccagccg   2700

caccgcggcg tcatcgaggc cgtctacctg cgcacacctt tctctgccgg taacgccacc   2760

acctaa                                                              2766
```

<210> SEQ ID NO 24
<211> LENGTH: 2757
<212> TYPE: DNA
<213> ORGANISM: simian adenovirus SV-11

<400> SEQUENCE: 24

```
atggccaccc catcgatgat gccgcagtgg tcttacatgc acatcgccgg ccaggacgcc     60

tcggagtacc tgagtcccgg cctcgtgcag tttgcccgcg ccaccgacac ctacttcagc    120

ttgggaaaca agtttagaaa ccccaccgtg gcccccaccc acgatgtgac cacggaccgc    180

tcgcagaggc tgaccctgcg ctttgtgccc gtagaccggg aggacaccgc gtactcttac    240

aaagtgcgct acacgctggc cgtaggggac aaccgagtgc tggacatggc cagcacctac    300

tttgacattc ggggggtgct ggatcgggga cccagcttca agccttactc cggcaccgct    360
```

```
tacaactgtc tggctcccaa gggcgcccct aacccttcag aatgggaagg gtcagacaac    420
aaaacacacg ttagaggtca agcgcccttt attagcgatg aaattacaaa ggagggcata    480
aaagtaggca ctgatactgg aaaccccgga caggcaattt atgctaaaaa agcttaccag    540
ccggaacccc aggtgggaga aacacaatgg aacagcgacg tgggaacaaa cgacaaagcg    600
gcaggacgaa ttttaaagaa aacaacaccc atggttccgt gctacgggtc ttacgccaag    660
cccacaaacg aagaaggggg gcaggctaca aaccaacaag tagatttgca gtttttctca    720
acgggtagct ccaatacaac tcccaaagtt gtgctgtatt ccgaagacgt ttctcttgaa    780
acgccagaca cccacctggt gtttaaacca acagttactg cgggcgtcac aaatgcagaa    840
gctttgttag cgcagcaagc tgctccgaat cgtccaaact acattgcatt cagagataac    900
ttcattggac ttatgtatta caacagtaca ggaaatatgg gagtgctggc cggtcaggct    960
tcgcagttga acgctgtagt ggatttgcaa gacagaaaca ctgaactgtc atatcagcta   1020
atgttggatg ctttaggtga cagaagcagg tacttttcaa tgtggaatca agccgtggac   1080
agttatgacc ctgatgtaag aattgtggaa aatcatggag tagaagacga attacccaac   1140
tattgttttc cgctgggggg catggcagtc accgatacct actcaggcat aaaaccttca   1200
gataacggag gtacatttca ggcagataac actgttgcag atagagtaga aataggttca   1260
ggaaacatgt tcgccatgga aatcaatttg caagccaacc tgtggcgggg tttcttatac   1320
tccaatatcg gactgtacct cccagacacg ctaaaactca cccctgacaa cattacgctg   1380
ccagaaaaca aaaataccta ccagtacatg aacggtcgag tcacacctcc cgggctcgtg   1440
gacacctacg tcaacgtggg tgcgcgctgg tcccccgatg tcatggacag cattaacccc   1500
ttcaaccacc accgcaacgc ggggctacgc taccgctcca tgttgctggg caacggccgc   1560
tacgtgccct tccacattca ggtgccccaa aaattctttg ccattaagaa cctgctgctg   1620
ctccccggtt cctataccta cgagtggaac ttccgcaagg acgtcaatat gatcttgcag   1680
agctcgctgg gcaatgacct gcgagtggac ggagccagca tccgcttcga cagcatcaac   1740
ctctacgcca actttttccc catggctcac aacacggcct ccaccctgga agccatgctg   1800
cgcaacgaca ccaacgacca atctttcaac gactacctgt gcgcggccaa catgctgtat   1860
cccatccccg ccaatgccac cagcgtgccc atctccattc cctctcgcaa ctgggcagcc   1920
ttcaggggct ggagttttac ccgcctcaaa accaaggaga ccccatcgct gggctccggg   1980
ttcgacccct actttgtgta ctccggaagc atcccctacc tggacggcac cttctacctc   2040
aaccatactt tcaaaaaggt gtccatcatg ttcgactcct cggtcagctg gcccggcaac   2100
gaccgcctgc tgacgcccaa cgagtttgag atcaagcgtt cggtagacgg tgaagggtac   2160
aacgtggccc agagcaacat gaccaaggac tggttcctga ttcagatgct gagccactac   2220
aacatcggct accagggctt ttacgtgccc gaaaattaca aggaccgcat gtactctttc   2280
ttcagaaact tccaacccat gagccgtcag gtggtagaca ccgttgccta ccagaacacg   2340
tatcaggacg tgaaactgcc ataccagcac aacaactcgg gtttcgtggg ttacatgggc   2400
cccaccatga gagagggtca ggcttacccg gccaactatc cctaccccct gatcggggcc   2460
accgccgtgc ccagtctgac gcagaaaaag ttcctctgcg accgggtgat gtggaggatc   2520
cccttctcta gcaacttcat gtcgatgggc tccctcaccg acctggggca gaacatgctg   2580
tacgccaact ccgctcacgc cttggatatg acctttgagg tggatcccat ggatgagccc   2640
acgcttctct atgttctgtt tgaagtcttc gacgtggtgc gcatccacca gccgcaccgc   2700
ggcgtcatcg aggccgtcta cctgcgcaca cctttctctg ccggtaacgc caccacc      2757
```

<210> SEQ ID NO 25
<211> LENGTH: 2760
<212> TYPE: DNA
<213> ORGANISM: simian adenovirus SV-16

<400> SEQUENCE: 25
atggccaccc cctcgatgat gccgcagtgg tcgtacatgc acatcgcggg ccaggacgcc 60
tcggagtacc tgagtcccgg tctggtgcag ttcgcccgcg ccaccgacac ttactttagc 120
ttgggcaaca agttcaggaa ccccacggtg gcgcccaccc acgacgtaac cacggaccgt 180
tcgcagcgcc tgacgctgcg attcgtcccc gtggaccgcg aggacaccgc gtactcttac 240
aaggcgcgtt tcacgctggc cgtgggcgac aaccgcgtgc tggacatggc cagcacgtac 300
tttgacatcc gcggcgttct ggaccgcggt cccagcttta agccctactc gggcaccgcc 360
tacaactgcc tggcccccaa aaccgctccc aacccttccg agtgggaggg aagcgataac 420
aaaattaacg tgagggggca agctccctac tttagccagg gtcttaccaa agatggtatt 480
caggtgggca ccgtgattga cgctacgtcg caagcaagcc aacctgtgta tgctaacccc 540
gcctatcagc cagaacctca ggtgggggaa aatcaatgga acagcgaggc gggaggagat 600
gacaaactgg cagggagagt gctgaaaaac agcaccccta tgtacccatg ctacggctcc 660
tacgccatgc ccaccaacgt tcaaggagga caaggagtag gcgatgtaac catgcaattt 720
tttgcaacaa caagtaccac caacacgcca aaggctgtat tgtacgctga agacgtagct 780
cttcaaactc cagatactca tatagtgttt aagcctgatg ttcccgcagg cacacaaaac 840
gctcaagctc tgctggccca gcaggcggcc cctaacagag ccaactacat tggatttaga 900
gataacttta ttgggcttat gtattacaac agcactggaa acatgggaat gctagctgga 960
caggcctccc aattaaatgc tgtggttgac ttgcaagaca gaaacaccga actgtcttac 1020
cagctcatgt tagatgcact gggagaccga agtcggtact tttccatgtg gaaccaggca 1080
gaagacagct acgatcccga tgtaagaatc attgaaaacc acggagtcga agacgagttg 1140
cctaactatt gttttccact gggaggcatg gcagtgacag acacatatac tgccataaaa 1200
ttaaatggcg atacaaattg ggctgccgac gacaccttta ataacagagt agaaattggt 1260
tcaggcaaca tgtttgccat ggaaattaac cttcaagcca acctgtggcg cagttttctt 1320
tattccaata ttggccttta tcttcctgac aacctaaagt acaccccaga caacataacg 1380
ctgcccacca accaaaacac gtacgcttac atgaatggtc gtgtgactcc gcccggtctt 1440
attgacactt atgtaaacat aggcgcccgc tggtccccag acgtgatgga caatgttaac 1500
cctttcaatc accatcgcaa tgcaggactg cgctatcggt ccatgttgct gggaaacggt 1560
cgatacgtgc ctttccatat tcaggtgccc caaaaattct ttgccattaa aaacctactg 1620
ctccttcccg gctcctacac ctacgaatgg aatttccgca aagacgtgaa catgatcttg 1680
cagagtacat taggtaacga cctgagagtg gacggagcct ccattcagtt tactagcatt 1740
aatctttatg ctaacttttt tcctatggct cacaacaccg cctccacttt ggaggccatg 1800
ctgcgcaacg acactaatga ccagtctttc aacgactacc tgtgcgcggc caacatgctc 1860
taccccattc ccgccaacgc caccagtgtg cccatatcta ttccgtcccg caactgggca 1920
gcttttagag gttggagctt cacgcggcta aaaaccaagg aaacgcctgc gttgggctct 1980
ggctttgatc cttattttgt gtattctggc actattccct accttgatgg cactttttac 2040
ttaaatcaca ctttcaaaaa agtgtctatt atgtttgact cctctgtgag ctggccgggt 2100
aacgaccgcc ttctcactcc caatgagttt gaaattaaac gctcggtgga tggagaaggt 2160

```
tacaacgtag cccaaagcaa catgaccaag gactggtttt tagttcagat gctgagcaac   2220
tacaacattg gttttcaggg attttacgtg cctgagaact acaaagaccg catgtattcc   2280
ttctttagaa actttcagcc catgagccgt caggttgtgg acactgtcaa ctacgccaac   2340
tacaaagaag taaccttagc ctaccaacat aataactcgg gttttgtggg ttacatggcc   2400
cccactatgc gagagggaca ggcctatccc gctaactttc catatcctct tattggaaac   2460
gacgctgtgc ctaaccaact gacacagaaa aagttcctct gcgaccgcat catgtggcgc   2520
attccgttct ccagcaactt catgtccatg gggcccctca ccgatctggg acagaacatg   2580
ttgtacgcca actcggcgca cgcgctggac atgacttttg aggtggatgc aatggacgag   2640
cccacccttc tttatgtttt gttcgaagtt ttcgacgtgg tgcgcattca ccagccgcac   2700
cgcggcgtca tcgaggccgt ctacctgcgc acgccgttct cggccggcaa cgccaccacc   2760
```

<210> SEQ ID NO 26
<211> LENGTH: 2751
<212> TYPE: DNA
<213> ORGANISM: simian adenovirus SV-18

<400> SEQUENCE: 26

```
atggccaccc cctcgatgat gccgcagtgg tcttacatgc acatcgccgg gcaggacgcc     60
tcggagtacc tgagcccggg cctggtgcag ttcgcccgcg ccaccgacac gtacttcagc    120
ctgggcaaca agtttaggaa ccccacggtg gcccccaccc acgacgtgac gacggaccgg    180
tcccagcggc tgacgctgcg gttcgtgccc gtcgaccgcg aggacaccgc gtactcgtac    240
aaagtgcgct tcacgctggc cgtgggcgac aaccgcgtgc tggacatggc cagcacgtac    300
tttgacatcc gcggcgtgtt ggaccgcggt cccagcttca aaccctactc cggcaccgcc    360
tacaactccc tggcccccaa gggcgccccc aacccgtcag aatggaaggg ctcagacaac    420
aaaattagtg taagaggtca ggctccgttt tttagtacat ccattacaaa ggatggtatt    480
caagtggcca ctgatacttc tagcggagct gtgtatgcta aaaaggaata tcagcctgaa    540
ccacaagtag ggcaagaaca atggaacagc gaagccagtg atagtgataa agtagctggt    600
aggattctaa aagacacaac acccatgttc ccttgttacg gttcctacgc caagcccaca    660
aatgaacagg gggggcaagg cactaatact gtagatctgc agttctttgc ctcttcatcg    720
gctacctcta cgcctaaagc cgtactctat gccgaggacg tggcaataga agcaccagac    780
acccatttgg tgtacaaacc ggcagttaca accacgacca ctagttccca agacctgcta    840
actcagcagg ctgctcccaa ccgacccaac tacattggct tcagggataa ttttatcggt    900
ctcatgtatt acaactccac tggcaatatg ggtgttttgg cagggcaagc ttctcagcta    960
aacgcagtgg ttgacttgca agacagaaac accgagctgt cctaccagct catgcttgat   1020
gctttgggcg accgcagtcg ttacttctcc atgtggaacc aggccgtaga cagctatgac   1080
cctgatgtca gaattattga aaatcatggt gtggaggatg agctgccaaa ctactgtttc   1140
ccgctaggag ggtcgctagt aactgaaact tatacaggcc tatcacccca aaacggaagt   1200
aacacgtgga caaccgacag caccacctat gcaactagag ggtggaaat cggctctggc   1260
aacatgttcg ccatggaaat taatttggcg gccaatctat ggaggagttt cctgtactcc   1320
aacgtggccc tgtacctgcc cgacgagtac aagctcaccc ccgacaacat caccctcccc   1380
gacaacaaaa acacttacga ctacatgaac ggccgcgtgg ccgcccccag ctccctcgac   1440
acctacgtca acatcggggc gcgctggtcc cccgacccca tggacaacgt caaccccttc   1500
aaccaccacc gcaacgcggg actgcgctac cgctccatgc tgctgggcaa cggccgctac   1560
```

```
gtacccttcc acatccaagt gccccagaaa ttcttcgcca tcaaaaacct cctgctcctc   1620
cccgggtcct acacctacga gtggaacttc cgcaaggacg tcaacatgat cctccagagc   1680
agcctgggta acgacctccg cgtcgacggg gccagcgtca ggttcgacag catcaacctg   1740
tacgccaact tcttccccat ggcccacaac accgcctcca cgctcgaggc catgctgcgc   1800
aacgacacca acgaccagtc gttcaacgac tacctctgcg ctgccaacat gctctacccc   1860
atccccgcca acgccaccag cgtgcccatc tccattccct cgcggaactg ggccgccttc   1920
cggggctgga gcttcacccg gctcaagacc aaggagaccc cctctctggg ctccggcttc   1980
gatccctact tcacctactc gggctccatc ccctacctgg acggcacctt ctacctcaac   2040
cacactttca agaaggtctc catcatgttc gactcctccg tcagctggcc cggcaacgac   2100
cgcctgctga cccccaacga gttcgagatc aagcgcaccg tggacgggga agggtacaac   2160
gtggcccagt gcaacatgac caaggactgg ttcctcatcc agatgctcag ccactacaac   2220
atcggctacc agggcttcta cgtgcccgag ggctacaagg acaggatgta ctctttcttc   2280
cgcaacttcc aacccatgag ccgccaggtg gtcgacacca ccacctacac cgactacaaa   2340
aacgtcaccc tcccctcca gcacaacaac tcggggttcg tgggatacat gggccccacc   2400
atgcgcgagg ggcaggccta ccccgccaac taccctacc ccctgatcgg caagaccgcc   2460
gtgcccagcc tcacgcagaa aaagttcctc tgcgaccgca ccatgtggcg catccccttc   2520
tccagtaact tcatgtccat gggggcgctc accgacctgg ggcagaacat gctgtacgcc   2580
aactccgccc acgccctcga catgaccttc gaggtggacc ccatggatga gcccacgctt   2640
ctctatgttc tgttcgaagt gttcgacgtc gtgcgcatcc accagccgca ccgcggcgtc   2700
atcgaggccg tctacctgcg cacgccgttc tcggccggta acgccaccac c            2751
```

<210> SEQ ID NO 27
<211> LENGTH: 2796
<212> TYPE: DNA
<213> ORGANISM: simian adenovirus SV-38

<400> SEQUENCE: 27

```
atggccaccc catcgatgat gccgcagtgg tcttacatgc acatcgccgg gcaggacgcc     60
tcggagtacc tgagtcccgg cctcgtgcag tttgcccgcg ccaccgacac ctacttcagc    120
ttgggaaaca agtttagaaa ccccaccgtg gccccccaccc acgatgtgac cacggaccgc    180
tcgcagaggc tgaccctgcg ttttgtgccc gtagaccggg aagacaccgc gtactcttac    240
aaagtgcgct tcaccctggc tgtaggagac aacagagtgt tggacatggc cagcacgtat    300
ttcgacattc gcggaatgtt agatcgcggt cccagcttta aaccctattc tggcaccgct    360
tacaactctt tagctcctaa aggcgctcca aacccgagtc agtggataac gaacgggga    420
acagcaaaaa ccaattcttt tgctcaagcg tcgtacatag gtatgggggc aaacctaaca    480
acaaacggca tccaagtggc agtagacaca aacaatgcca acgccgcggt gtacgcgaat    540
aagatttacc agccagagcc tcaagttgga acatcacaat ggaatctgaa tcctacgcaa    600
aatgccgcgg gaagaattct aaaaccaaca accccaatgc aaccttgcta cggttcctac    660
gcttacccta ctaatgaaaa cggcggtcaa gtaaaaatta ccgatggtac aacggaccca    720
actggcgcaa acagcgtcag catggagttt ttcacaacca ccgccgataa ccagaatcaa    780
gctaaggttg tactgtacag cgaagacgtt aatttggaag cgcctgacac ccacttggtt    840
tttaaacccg acgttgcaga taatgcaaaa gctgcagaaa cccttctagg gcagcagtcc    900
gctcccaaca gacccaatta cattggattc agagataact ttatcggtct aatgtattac    960
```

```
aactcaactg gaaatatggg agtgttggca ggtcaagcgt ctcagttaaa cgcagttgtg   1020

gacttgcaag acagaaacac cgaattgtca taccagctta tgctcgacgc attgggagac   1080

agaagtcgat acttttcaat gtggaatcaa gctgtcgaca gttacgatcc agatgttagg   1140

ataattgaaa accacggcgt tgaagacgag cttccaaatt attgttttcc actaaatgga   1200

cagggaattt caaacaccta caaggggctg tctgtacaaa atggacaaaa cacatggcag   1260

gctaacaaca acgctgccga aaacaatgaa atttccatcg gcaacatttt tgcgatggaa   1320

ataaatttgg cagctaattt gtggcgcagt ttctatact ccaatgttgc cctgtacttg   1380

ccagactcct acaagtacac ccctgacaac attgaacttc caacaaacca aaacagctac   1440

ggctacatta acggcagggt tactgccccc aacgctattg atacatatgt caatattggc   1500

gcccgttggt ctcccgatcc catggacaac gttaaccctt ttaatcacca ccgcaacgcc   1560

ggtctgcgct atcgctctat gctcctaggt aacggccggt acgtaccctt ccacattcag   1620

gtgccccaga aattttttgc tattaagaat ctgcttttac tgcctgggtc ttacacctac   1680

gaatggaact tcagaaaaga tgtgaacatg atcttgcaga gcactctggg caacgacctg   1740

cgtgtcgacg gggctagcgt taaattcgac agcattaacc tctacgcaaa tttttcccc   1800

atggcccaca acacggcttc caccctggag gccatgctgc gcaacgacac caacgaccag   1860

tccttcaacg actacctgtg cgcagctaac atgctgtacc ccatccccgc aaacgccacc   1920

agcgtgccca tctctattcc ctctcgcaac tgggcagcct taggggctg gagttttacc   1980

cgccttaaaa ccaaggaaac tccctcgctg ggctccggtt ttgacccta ctttgtctac   2040

tccggctcca ttccctacct ggacggcacc ttttacctca accacacttt taaaaaggtg   2100

tccatcatgt ttgactcatc ggtcagctgg cccggcaacg accgcctgct aacgcccaac   2160

gagttcgaaa ttaagcgttc ggtagacggt gaagggtaca acgtggccca aagcaacatg   2220

accaaggact ggttcctgat tcaaatgctc agccactaca acatcggcta ccagggcttc   2280

tacgtgcccg aaaactacaa ggaccgcatg tactccttct tcagaaactt ccaacctatg   2340

agtcggcagg tggtagactc ggttaactat gctaactaca aggaagtaaa aatgccattc   2400

cagcacaata actccggctt tgtggggtac atgggaccta ccatgagaga aggacaggcc   2460

tacccggcca attatccata tcccctaatt ggccaaaccg ccgttcccag tctcacgcaa   2520

aaaaagttcc tctgcgaccg ggtgatgtgg aggatcccct tctctagcaa cttcatgtct   2580

atgggctccc tcaccgacct ggggcagaac atgctgtacg ccaactccgc tcacgccttg   2640

gatatgacct ttgaggtgga tcccatggat gagcccacgc ttctctatgt tctgtttgaa   2700

gttttcgacg tggtgcgcat ccaccagccg caccgcggcg tcatcgaggc cgtctacctg   2760

cgcacacctt tctctgccgg taacgccacc acctaa                             2796
```

<210> SEQ ID NO 28
<211> LENGTH: 1726
<212> TYPE: DNA
<213> ORGANISM: simian adenovirus SV-39

<400> SEQUENCE: 28

```
agtttgcccg tgcgacggaa acctacttct cactgggcaa caagttcagg aaccccaccg     60

tggcgcccac ccacgacgtc accaccgatc ggtcccagcg actgacaatc cgcttcgtcc    120

ccgtggacaa ggaagacacc gcttactcct acaaaacccg cttcacgctg gccgtgggcg    180

acaaccgggt gctagacatg gccagtacct actttgacat ccgcggcgtg atcgaccgcg    240

gacctagctt caagccttac tccggcacgg cttacaactc actggctccc aaaggggcgc    300
```

-continued

```
ccaacaacag ccaatggaac gccacagata acgggaacaa gccagtgtgt tttgctcagg    360
cagcttttat aggtcaaagc attacaaaag acggagtgca aatacagaac tcagaaaatc    420
aacaggctgc tgccgacaaa acttaccaac cagagcctca aattggagtt tccacctggg    480
ataccaacgt taccagtaac gctgccggac gagtgttaaa agccaccact cccatgctgc    540
catgttacgg ttcatatgcc aatcccacta atccaaacgg gggtcaggca aaaacagaag    600
gagacatttc gctaaacttt ttcacaacaa ctgcggcagc agacaataat cccaaagtgg    660
ttctttacag cgaagatgta aaccttcaag cccccgatac tcacttagta tataagccaa    720
cggtgggaga aaacgttatc gccgcagaag ccctgctaac gcagcaggcg tgtcccaaca    780
gagcaaacta cataggtttc cgagataact ttatcggttt aatgtattat aacagcacag    840
ggaacatggg agttctggca ggtcaggcct cgcagttaaa cgcagttgta gacctgcaag    900
atcgaaacac ggaactgtcc tatcagctaa tgctagatgc tctgggtgac agaactcgat    960
atttctcaat gtggaatcag gccgtggaca gctacgatcc agacgttagg attatcgaga   1020
accatggggt ggaagacgag ctgcccaatt actgttttcc actcccaggc atgggtattt   1080
ttaactccta caagggggta aaaccacaaa atggcggtaa tggtaactgg gaagcaaacg   1140
gggacctatc aaatgccaat gagatcgctt taggaaacat ttttgccatg gaaattaacc   1200
tccacgcaaa cctgtggcgc agcttcttgt acagcaatgt ggcgctgtac ctgccagaca   1260
gctataaatt cactcccgct aacatcactc tgcccgccaa ccaaaacacc tacgagtata   1320
tcaacgggcg cgtcacttct ccaaccctgg tggacacctt tgttaacatt ggagcccgat   1380
ggtcgccgga tcccatggac aacgtcaacc cctttaacca tcaccggaac gcgggcctcc   1440
gttaccgctc catgctgctg ggaaatggac gcgtggtgcc tttccacata caagtgccgc   1500
aaaaattttt cgcgattaag aacctcctgc ttttgcccgg ctcctacact tacgagtgga   1560
gcttcagaaa agacgtgaac atgattctgc agagcaccct gggcaatgat cttcgagtgg   1620
acggggccag cgtccgcatt gacagcgtca acttgtacgc caactttttc cccatggcgc   1680
acaacaccgc ttctaccttg gaagccatgc tgcgaaacga caccaa                  1726
```